US008357511B2

(12) United States Patent
Brown et al.

(10) Patent No.: US 8,357,511 B2
(45) Date of Patent: Jan. 22, 2013

(54) PROTEIN PURIFICATION TAGS AND USES THEREOF

(75) Inventors: William Clay Brown, Chelsea, MI (US); James E. Delproposto, Ann Arbor, MI (US); Janet Smith, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 54 days.

(21) Appl. No.: 13/055,199

(22) PCT Filed: Jul. 31, 2009

(86) PCT No.: PCT/US2009/052440
§ 371 (c)(1),
(2), (4) Date: Mar. 3, 2011

(87) PCT Pub. No.: WO2010/014922
PCT Pub. Date: Feb. 4, 2010

(65) Prior Publication Data
US 2011/0165624 A1 Jul. 7, 2011

Related U.S. Application Data

(60) Provisional application No. 61/085,648, filed on Aug. 1, 2008.

(51) Int. Cl.
*C12P 21/00* (2006.01)
*C12N 15/00* (2006.01)
*C12N 1/20* (2006.01)
*C07K 1/00* (2006.01)

(52) U.S. Cl. .................... 435/69.1; 530/350; 435/252.3; 435/320.1

(58) Field of Classification Search ................ 435/69.1, 435/252.3, 320.1; 536/23.1
See application file for complete search history.

(56) References Cited s

OTHER PUBLICATIONS

M.D Walkinshaw et al., "Structure of Ocr from Bacteriophage T7, a Protein that mimics B-Form DNA" Molecular Cell 2002, 9(1): 187-194.
Atanasiu et al., "Characterization of the structure of ocr, the gene 0.3 protein of bacteriophage T7." Nucleic Acids Research 2001, 29(14):3059-3068.
Deloproposto et al., "Mocr: a novel fusion tag for the enhancing solubility that is compatible with structural biology applications." Protein Expression and Purification 2008, 63(1):40-49.
GenBank Accession No. AAP33909, 'gene 0.3 [Enterobacteria phage T7]' Nov. 14, 2003.
GenBank Accession No. AAC31993, 'protein 0.3 [Enterobacteria phage T7]', Aug. 17, 1998.
GenBank Accession No. AY264774, 'Enterobacteria phage T7, complete genome', Nov. 14, 2003.
Waugh, "Making the most of affinity tags."TRENDS in Biotechnology (2005), 23:316-320.
Terpe, "Overview of tag protein fusions: from molecular and biochemical fundamentals to commercial systems." Appl. Microbiol. Biotechnol. 2003, 60:523-533.
Esposito and Chattergee, "Enhancement of soluble protein expression through the use of fusion tags." Curr. Opin. Biotechnology 2006, 17:353-358.
Kapust and Waugh, "*Escherichia coli* maltose-binding protein is uncommonly effective at promoting the solubility of polypeptides to which it is fused." Protein Science 1999, 8:1668-1674.
Hammarstrom et al., "Rapid screening for improved solubility of small human proteins produced as fusion proteins in *Escherichia coli*." Protein Science 2002, 11:313-321.
Fox et al., "Maltodextrin-binding proteins from diverse bacteria and archaea are potent solubility enhancers." FEBS Letters 2003, 537:53-57.
Su et al., "The acidity of protein fusion partners predominantly determines the efficacy to improve the solubility of the target proteins expressed in *Escherichia coli*." J. Biotechnology 2007, 129:373-382.
Pryor and Leiting, "High-Level Expression of Soluble Protein in *Escherichia coli* Using a His 6-Tag and Maltose-Binding-Protein Binding-Protein Double-Affinity Fusion System." Protein Expr. Purif. 1997, 10:309-319.
Chattergee and Esposito, "Enhanced soluble protein expression using two new fusion tags." Protein Expr. Purif. 2006, 46:122-129.
Nallamsetty and Waugh, "Mutations that alter the equilibrium between open and closed conformations of *Escherichia coli* maltose-binding protein impede its ability to enhance the solubility of passenger proteins." Biochem. Biophys. Res. Commun. 2007, 364:639-644.
Wilkinson and Harrison, "Predicting the solubility of recombinant proteins in *Escherichia coli*." Biotechnology 1991, 9:443-448.
Davis et al., "New fusion protein systems designed to give soluble expression in *Escherichia coli*" Biotechnol. Bioeng. 1999, 65:382-388.
Zhang et al., "Protein aggregation during overexpression limited by peptide extensions with large net negative charge." Protein Expr. Purif. 2004, 36(2):207-216.
Huth et al., "Design of an expression system for detecting folded protein domains and mapping macromolecular interactions by NMR." Protein Science 1997, 6:2359-2364.
Koenig ET A., "A rapid method to attain isotope labeled small soluble peptides for NMR studies." J. of Biomolecular NMR 2003, 26:193-202.
Sorenson et al., "A favorable solubility partner for the recombinant expression of streptavidin." Protein Expr. Purif. 2003, 32:252-259.
Smyth et al. "Crystal structures of fusion proteins with large-affinity tags." Protein Science 2003, 12:1313-1322.
Carrio et al., "Amyloid-like properties of bacterial inclusion bodies." J. Mol. Biol. 2005, 347:1025-1037.
Sabate and J. Estelrich, "Disaggregating effects of ethanol at low concentration on beta-poly-L-lysines." Int. J. of Biol. Macromol. 2003, 32:10-16.
Mark and Studier, "Purification of the gene 0.3 protein of bacteriophage T7, an inhibitor of the DNA restriction system of *Escherichia coli*." J. Biol. Chem. 1981, 256(5):2573-2578.
Kobe et al., "Crystal structure of human T cell leukemia virus type 1 gp21 ectodomain crystallized as a maltose-binding protein chimera reveals structural evolution of retroviral transmembrane proteins." Proc. Natl. Acad. Sci. 1999, 96:4319-4324.

(Continued)

*Primary Examiner* — Maryam Monshipouri
(74) *Attorney, Agent, or Firm* — Casimir Jones SC

(57) ABSTRACT

The present invention relates to fusion proteins. In particular, the present invention relates to protein tags for use in protein solubilization and purification.

26 Claims, 22 Drawing Sheets

OTHER PUBLICATIONS

Nagai et al., "Generation of beta-globin by sequence-specific proteolysis of a hybrid protein produced in *Escherichia coli*." Nature 1984, 309(5971):810-812.

Kruger et al., "Active protection by bacteriophages T3 and T7 against *E. coli* B- and K-specific restriction of their DNA." Mol. Gen. Genet. 1977, 153:99-106.

Fernandez et al., "Mechanism of caveolin filament assembly." Proc. Natl. Acad. Sci. 2002, 99:11193-1198.

Davidson et al., "Evidence for the biosynthesis of bryostatins by the bacterial symbiont "Candidatus Endobugula sertula" of the bryozoan *Bugula neritina*." Appl. Environ. Microbiol. 2001, 67:4531-4537.

Bjorklund and Gustafsson, "The yeast mediator complex and its regulation." TRENDS in Biochemical Sciences 2006, 30:240-244.

FIGURE 3

MHHHHHHSSGVDLAMSNMTTNNYFDHAYEMLKENIRYDDIRDTDDLHDAIHMAADNAVPHYYADIRSV
MASEGIDLEFEDSGLMPDTKDDIRILQARIYEQLTIDLWEDAEDLLNEYLEEVEEYEEDEEGTENLYFQSNI
GSG*

FIGURE 13

SEQ ID NO:2

AMSNMTYNNVFDHAYEMLKENIRYDDIR
DTDDLHDAIHMAADNAVPHYYADIRSVM
ASEGIDLEFEDSGLMPDTKDDIRILQARIYE
QLTIDLWEDAEDLLNEYLEEVEEYEEDEE

FIGURE 15

SEQ ID NO:16

*MHHHHHHSSGVDL*MAMSNMTYNNVFDHAYEMLKENIRYDD
IRDTDDLHDAIHMAADNAVPHYYADIRSVMTSEGIDLEFEDSGL
MPDTKDDIRILQARIYEQLTIDLWEDAEDLLNEYLE<u>EVEEYEEDEE</u>
*GTENLYFQSNA*

Bold: Mocr amino acids
*Italic*: amino acids contributed by vector, removed in crystallization construct
<u>Underlined</u>: disordered region in Ocr structure, removed in crystallization construct

```
                      BsaT1101        ApaI
                      AvaI            EcoRI
                      SmlI                        OxaII
                      XhoI        BamHI           HindIII
                                  XhoII
aac  gaa  tac  ctc gag  aac  gga tcc  gaa ttc  gac aag ctt  gtc
ttg  ctt  atg  gag ctc  ttg  cct agg  ctt aag  ctg ttc gaa  cag
 N    E    Y    L   E    N    G   S    E   F    D   K   L    V
```

Downstream cloning sites: BamHI, EcoRI, HindIII

Fig. 16

SEQ ID NO:1

Mocr DNA sequence lacking Met translation initiation codon

GCTATGTCTAACATGACTTACAACAACGTATTCGACCACGCTTATGAAATGCTGAAA
GAAAACATCCGTTATGATGATATCCGCGATACTGACGACCTTCACGATGCTATTCAC
ATGGCTGCAGATAATGCAGTTCCGCACTACTATGCTGACATCCGTAGCGTAATGGCA
AGTGAGGGCATTGACCTTGAGTTTGAAGATTCCGGTCTGATGCCTGACACCAAGGAC
GACATCCGCATACTACAGGCTCGTATCTATGAACAATTAACGATTGACCTCTGGGAA
GATGCTGAGGACTTGCTGAACGAATACTTGGAAGAGGTAGAGGAGTACGAGGAGGA
TGAA

SEQ ID NO:2

Mocr amino acid sequence lacking initiation Met

AMSNMTYNNVFDHAYEMLKENIRYDDIRDTDDLHDAIHMAADNAVPHYYADIRSVMA
SEGIDLEFEDSGLMPDTKDDIRILQARIYEQLTIDLWEDAEDLLNEYLEEVEEYEEDEE

SEQ ID NO:3

Mocr DNA sequence including Met translation initiation codon

ATGGCTATGTCTAACATGACTTACAACAACGTATTCGACCACGCTTAT
GAAATGCTGAAAGAAAACATCCGTTATGATGATATCCGCGATACTGAC
GACCTTCACGATGCTATTCACATGGCTGCAGATAATGCAGTTCCGCAC
TACTATGCTGACATCCGTAGCGTAATGGCAAGTGAGGGCATTGACCTT
GAGTTTGAAGATTCCGGTCTGATGCCTGACACCAAGGACGACATCCGC
ATACTACAGGCTCGTATCTATGAACAATTAACGATTGACCTCTGGGAA
GATGCTGAGGACTTGCTGAACGAATACTTGGAAGAGGTAGAGGAGTA
CGAGGAGGATGAA

Fig. 16 CONT.

SEQ ID NO:4

Mocr DNA sequence including initiation Met

MAMSNMTYNNVFDHAYEMLKENIRYDDIRDTDDLHDAIHMAADNAVP
HYYADIRSVMASEGIDLEFEDSGLMPDTKDDIRILQARIYEQLTIDLWEDA
EDLLNEYLEEVEEYEEDEE

SEQ ID NO:5

Acidic Mocr DNA sequence

ATGGCTATGAGCGACATGACCTACAACGACGTCTTCGACGATGCATATGAAATGCTG
AAAGAAGACATTCGTGAAGACGATATCGATGACACCGATGATCTGGACGATGCGAT
CGATGATGCAGCCGATGACGCCGTGCCGGATGATTACGACGATATTCGCGACGTCAT
GGACTCTGAGGGTATTGACCTGGAGTTTGAAGACGATGATCTGATGCCGGATACCG
ACGATGACATCGAAATCCTGCAGGACCGCATCTACGAGGAACTGACCGATGACCTG
TGGGAAGATGCAGAAGACCTGCTGGATGAATATCTGGAAGAGGTGGAAGAATACGA
AGAGGACGAGGAA

SEQ ID NO:6

Acidic Mocr amino acid sequence

MAMSDMTYNDVFDDAYEMLKEDIREDDIDDTDDLDDAIDDAADDAVPDDYDDIRDV
MDSEGIDLEFEDDDLMPDTDDDIEILQDRIYEELTDDLWEDAEDLLDEYLEEVEEYEEDE
E

Fig. 16 CONT.

SEQ ID NO:7
Basic Mocr DNA sequence
ATGGCGATGTCCAACATGACTTATAATAACGTATTCAACCGTGCGTATCGTAAGCTG
AAACAGAACATCCGTCGTAATAACATCCGTAATACCCGCAACCTGCACAACGCTAT
CCACAAAGCTGCTAACAACGCGGTTCCGCACCGTTACCGCAACATCCGCAGCGTCAT
GCGCTCCCAGGGCATTAATCGTCAGTTCCAGAACTCTGGCCTGATGCCGAATACCAA
AAATGACATCCGTATCCTGCAGGCTCGTATTTACGAACAACTGACCATCGACCTGTG
GGAGGACGCCGAAGACCTGCTGAACGAATACCTGCAACAGGTACAGCAGTATCAGC
AGAACCAACAG SEQ ID NO:8
Basic Mocr amino acid sequence
MAMSNMTYNNVFNRAYRKLKQNIRRNNIRNTRNLHNAIHKAANNAVPHRYRNIRSVM
RSQGINRQFQNSGLMPNTKNDIRILQARIYEQLTIDLWEDAEDLLNEYLQQVQQYQQNQ
Q SEQ ID NO:9
Serine-rich Mocr DNA sequence
ATGGCTATGTCTAATATGACTTACAACTCTGTTTTCTCTTCCGCGTACTCTATGCTGA
AAGCTCCATCCGTTCTAGCTCCATCAGCTCCTCTTCTTCCCTGTCTAGCGCCATCTC
CAGCGCAGCGTCCAGCGCAGTGCCGTCCAGCTACAGCAGCATTCGCTCTGTCATGTC
TAGCAGCGGCATCTCCTCCTCCTTCTCTTCTTCCCTGATGCCGAGCACGAGCTCT
GATATCAGCATTCTGCAGGCGCGCATTTATGAAAGCCTGACTAGCAGCCTGTGGTCT
AGCGCTAGCTCTCTGCTGTCTTCTTATCTGGAAGAAGTTGAAGAATATGAGGAAGAC
GAAGAA

Fig. 16 CONT.

SEQ ID NO:10

Serine-rich Mocr amino acid sequence

MAMSNMTYNSVFSSAYSMLKSSIRSSSISSSSSLSSAISSAASSAVPSSYSSIRSVMSSS
GISSSFSSSSLMPSTSSDISILQARIYESLTSSLWSSASSLLSSYLEEVEEYEEDEE

SEQ ID NO:11

Tagged crystallization Mocr DNA sequence atgcaccatcatcatcatcatcttctggtgtagatctgGCAATGTCTAACATGACTTACAACAACGTATTCG
ACCACGCTTATGAAATGCTGAAAGAAAACATCCGTTATGATGATATCCGCGATACTG
ACGACCTTCACGATGCTATTCACATGGCTGCAGATAATGCAGTTCCGCACTACTATG
CTGACATCCGTAGCGTAATGGCAAGTGAGGGCATTGACCTTGAGTTTGAAGATTCCG
GTCTGATGCCTGACACCAAGGACGACATCCGCATACTACAGGCTCGTATCTATGAA
CAATTAACGATTGACCTCTGGGAAGATGCTGAGGACTTGCTGAACGAATA
CCTCGAG

SEQ ID NO:12

Tagged crystallization Mocr amino acid sequence

MHHHHHHSSGVDLAMSNMTYNNVFDHAYEMLKENIRYDDIRDTDDLHDAI
HMAADNAVPHYYADIRSVMASEGIDLEFEDSGLMPDTKDDIRILQARIYE
QLTIDLWEDAEDLLNEYLE

Fig. 16 CONT.

SEQ ID NO:13

Untagged crystallization Mocr DNA sequence

ATGGCAATGTCTAACATGACTTACAACAACGTATTCGACCACGCTTATGAAAT
GCTGAAAGAAAACATCCGTTATGATGATATCCGCGATACTGACGACCTTC
ACGATGCTATTCACATGGCTGCAGATAATGCAGTTCCGCACTACTATGCT
GACATCCGTAGCGTAATGGCAAGTGAGGGCATTGACCTTGAGTTTGAAGA
TTCCGGTCTGATGCCTGACACCAAGGACGACATCCGCATACTACAGGCTC
GTATCTATGAACAATTAACGATTGACCTCTGGGAAGATGCTGAGGACTTG
CTGAACGAATACCTCGAG

SEQ ID NO:14

Untagged crystallization Mocr amino acid sequence

MAMSNMTYNNVFDHAYEMLKENIRYDDIRDTDDLHDAI
HMAADNAVPHYYADIRSVMASEGIDLEFEDSGLMPDTKDDIRILQARIYE
QLTIDLWEDAEDLLNEYLE

SEQ ID NO:15

Protein product of Mocr in the pMCSG7 vector

MHHHHHHSSGVDLAMSNMTYNNVFDHAYEMLKENIRYDDIRDTDDLHDAI
HMAADNAVPHYYADIRSVMASEGIDLEFEDSGLMPDTKDDIRILQARIYE
QLTIDLWEDAEDLLNEYLEEVEEYEEDEEGTENLYFQSNICSG*

Fig. 16 CONT.

SEQ ID NO:16

Mocr amino acid sequence with rigid linker region

MHHHHHHSSGVDLMAMSNMTYNNVFDHAYEMLKENIRYDDIRDTDDLHDAI
HMAADNAVPHYYADIRSVMTSEGIDLEFEDSGLMPDTKDDIRILQARIYE
QLTIDLWEDAEDLLNEYLEEVEEYEEDEEGTENLYFQSNA

SEQ ID NO:17

ATCGAGGGTAGG

SEQ ID NO:18

Ile-Glu-Gly-Arg

SEQ ID NO:19

TACTTCCAATCCAATGCN

SEQ ID NO:20

TTATCCACTTCCAATGTTA

SEQ ID NO:21

TTATCCACTTCCAATGCTA

Fig. 16 CONT.

SEQ ID NO:22

Ocr nucleic acid sequence

GCTATGTCTAACATGACTTACAACAACGTTTTCGACCACGCTTACGAAATGCTGAAA
GAAAACATCCGTTATGATGACATCCGTGACACTGATGACCTGCACGATGCTATTCAC
ATGGCTGCCGATAATGCAGTTCCGCACTACTACGCTGACATCTTTAGCGTAATGGCA
AGTGAGGGCATTGACCTTGAGTTCGAAGACTCTGGTCTGATGCCTGACACCAAGGAC
GTAATCCGCATCCTGCAAGCGCGTATCTATGAGCAATTAACGATTGACCTCTGGGAA
GACGCAGAAGACTTGCTCAATGAATACTTGGAGGAAGTCGAGGAGTACGAGGAGGA
TGAAGAG

SEQ ID NO:23

Ocr amino acid sequence

AMSNMTYNNVFDHAYEMLKENIRYDDIRDTDDLHDAIHMAADNAVPHYYADIFSVMA
SEGIDLEFEDSGLMPDTKDVIRILQARIYEQLTIDLWEDAEDLLNEYLEEVEEYEEDEE

```
                         SEQUENCE LISTING

<160> NUMBER OF SEQ ID NOS: 23

<210> SEQ ID NO 1
<211> LENGTH: 345
<212> TYPE: DNA
<213> ORGANISM: Artificial Sequence
<220> FEATURE:
<223> OTHER INFORMATION: Synthetic

<400> SEQUENCE: 1
gctatgtcta acatgactta caacaacgta ttcgaccacg cttatgaaat gctgaaagaa      60
aacatccgtt atgatgatat ccgcgatact gacgaccttc acgatgctat tcacatggct     120
gcagataatg cagttccgca ctactatgct gacatccgta gcgtaatggc aagtgagggc     180
attgaccttg agtttgaaga ttccggtctg atgcctgaca ccaaggacga catccgcata     240
ctacaggctc gtatctatga acaattaacg attgacctct gggaagatgc tgaggacttg     300
ctgaacgaat acttggaaga ggtagaggag tacgaggagg atgaa                     345

<210> SEQ ID NO 2
<211> LENGTH: 116
<212> TYPE: PRT
<213> ORGANISM: Artificial Sequence
<220> FEATURE:
<223> OTHER INFORMATION: Synthetic

<400> SEQUENCE: 2

Ala Met Ser Asn Met Thr Tyr Asn Asn Val Phe Asp His Ala Tyr Glu
1               5                   10                  15

Met Leu Lys Glu Asn Ile Arg Tyr Asp Asp Ile Arg Asp Thr Asp Asp
            20                  25                  30

Leu His Asp Ala Ile His Met Ala Ala Asp Asn Ala Val Pro His Tyr
        35                  40                  45

Tyr Ala Asp Ile Arg Ser Val Met Ala Ser Glu Gly Ile Asp Leu Glu
    50                  55                  60

Phe Glu Asp Ser Gly Leu Met Pro Asp Thr Lys Asp Asp Ile Arg Ile
65                  70                  75                  80

Leu Gln Ala Arg Ile Tyr Glu Gln Leu Thr Ile Asp Leu Trp Glu Asp
                85                  90                  95

Ala Glu Asp Leu Leu Asn Glu Tyr Leu Glu Glu Val Glu Glu Tyr Glu
            100                 105                 110

Glu Asp Glu Glu
        115

<210> SEQ ID NO 3
<211> LENGTH: 348
<212> TYPE: DNA
<213> ORGANISM: Artificial Sequence
<220> FEATURE:
<223> OTHER INFORMATION: Synthetic

<400> SEQUENCE: 3
atggctatgt ctaacatgac ttacaacaac gtattcgacc acgcttatga aatgctgaaa      60
```

```
gaaaacatcc gttatgatga tatccgcgat actgacgacc ttcacgatgc tattcacatg    120
gctgcagata atgcagttcc gcactactat gctgacatcc gtagcgtaat ggcaagtgag    180
ggcattgacc ttgagtttga agattccggt ctgatgcctg acaccaagga cgacatccgc    240
atactacagg ctcgtatcta tgaacaatta acgattgacc tctgggaaga tgctgaggac    300
ttgctgaacg aatacttgga agaggtagag gagtacgagg aggatgaa                 348
```

```
<210> SEQ ID NO 4
<211> LENGTH: 117
<212> TYPE: PRT
<213> ORGANISM: Artificial Sequence
<220> FEATURE:
<223> OTHER INFORMATION: Synthetic

<400> SEQUENCE: 4
```

```
Met Ala Met Ser Asn Met Thr Tyr Asn Asn Val Phe Asp His Ala Tyr
1               5                   10                  15

Glu Met Leu Lys Glu Asn Ile Arg Tyr Asp Asp Ile Arg Asp Thr Asp
            20                  25                  30

Asp Leu His Asp Ala Ile His Met Ala Ala Asp Asn Ala Val Pro His
        35                  40                  45

Tyr Tyr Ala Asp Ile Arg Ser Val Met Ala Ser Glu Gly Ile Asp Leu
    50                  55                  60

Glu Phe Glu Asp Ser Gly Leu Met Pro Asp Thr Lys Asp Ile Arg
65                  70                  75                  80

Ile Leu Gln Ala Arg Ile Tyr Glu Gln Leu Thr Ile Asp Leu Trp Glu
                85                  90                  95

Asp Ala Glu Asp Leu Leu Asn Glu Tyr Leu Glu Glu Val Glu Glu Tyr
            100                 105                 110

Glu Glu Asp Glu Glu
        115
```

```
<210> SEQ ID NO 5
<211> LENGTH: 351
<212> TYPE: DNA
<213> ORGANISM: Artificial Sequence
<220> FEATURE:
<223> OTHER INFORMATION: Synthetic

<400> SEQUENCE: 5
```

```
atggctatga gcgacatgac ctacaacgac gtcttcgacg atgcatatga aatgctgaaa     60
gaagacattc gtgaagacga tatcgatgac accgatgatc tggacgatgc gatcgatgat    120
gcagccgatg acgccgtgcc ggatgattac gacgatattc gcgacgtcat ggactctgag    180
ggtattgacc tggagtttga agacgatgat ctgatgccgg ataccgacga tgacatcgaa    240
atcctgcagg accgcatcta cgaggaactg accgatgacc tgtgggaaga tgcagaagac    300
ctgctggatg aatatctgga agaggtggaa gaatacgaag aggacgagga a             351
```

```
<210> SEQ ID NO 6
<211> LENGTH: 117
<212> TYPE: PRT
<213> ORGANISM: Artificial Sequence
<220> FEATURE:
<223> OTHER INFORMATION: Synthetic

<400> SEQUENCE: 6
```

```
Met Ala Met Ser Asp Met Thr Tyr Asn Asp Val Phe Asp Asp Ala Tyr
1               5                   10                  15

Glu Met Leu Lys Glu Asp Ile Arg Glu Asp Asp Ile Asp Asp Thr Asp
```

```
                      20                  25                  30
Asp Leu Asp Asp Ala Ile Asp Asp Ala Ala Asp Ala Val Pro Asp
         35                  40                  45

Asp Tyr Asp Asp Ile Arg Asp Val Met Asp Ser Glu Gly Ile Asp Leu
 50                  55                  60

Glu Phe Glu Asp Asp Leu Met Pro Asp Thr Asp Asp Ile Glu
65                  70                  75                  80

Ile Leu Gln Asp Arg Ile Tyr Glu Glu Leu Thr Asp Asp Leu Trp Glu
                 85                  90                  95

Asp Ala Glu Asp Leu Leu Asp Glu Tyr Leu Glu Glu Val Glu Glu Tyr
             100                 105                 110

Glu Glu Asp Glu Glu
         115

<210> SEQ ID NO 7
<211> LENGTH: 351
<212> TYPE: DNA
<213> ORGANISM: Artificial Sequence
<220> FEATURE:
<223> OTHER INFORMATION: Synthetic

<400> SEQUENCE: 7
atggcgatgt ccaacatgac ttataataac gtattcaacc gtgcgtatcg taagctgaaa      60
cagaacatcc gtcgtaataa catccgtaat acccgcaacc tgcacaacgc tatccacaaa    120
gctgctaaca acgcggttcc gcaccgttac cgcaacatcc gcagcgtcat gcgctcccag    180
ggcattaatc gtcagttcca gaactctggc ctgatgccga ataccaaaaa tgacatccgt    240
atcctgcagg ctcgtatttta cgaacaactg accatcgacc tgtgggagga cgccgaagac    300
ctgctgaacg aatacctgca acaggtacag cagtatcagc agaaccaaca g             351

<210> SEQ ID NO 8
<211> LENGTH: 117
<212> TYPE: PRT
<213> ORGANISM: Artificial Sequence
<220> FEATURE:
<223> OTHER INFORMATION: Synthetic

<400> SEQUENCE: 8

Met Ala Met Ser Asn Met Thr Tyr Asn Asn Val Phe Asn Arg Ala Tyr
1                5                  10                  15

Arg Lys Leu Lys Gln Asn Ile Arg Arg Asn Asn Ile Arg Asn Thr Arg
             20                  25                  30

Asn Leu His Asn Ala Ile His Lys Ala Ala Asn Asn Ala Val Pro His
         35                  40                  45

Arg Tyr Arg Asn Ile Arg Ser Val Met Arg Ser Gln Gly Ile Asn Arg
     50                  55                  60

Gln Phe Gln Asn Ser Gly Leu Met Pro Asn Thr Lys Asn Asp Ile Arg
65                  70                  75                  80

Ile Leu Gln Ala Arg Ile Tyr Glu Gln Leu Thr Ile Asp Leu Trp Glu
                 85                  90                  95

Asp Ala Glu Asp Leu Leu Asn Glu Tyr Leu Gln Gln Val Gln Gln Tyr
             100                 105                 110

Gln Gln Asn Gln Gln
         115

<210> SEQ ID NO 9
<211> LENGTH: 351
<212> TYPE: DNA
```

<213> ORGANISM: Artificial Sequence
<220> FEATURE:
<223> OTHER INFORMATION: Synthetic

<400> SEQUENCE: 9

```
atggctatgt ctaatatgac ttacaactct gttttctctt ccgcgtactc tatgctgaaa      60
agctccatcc gttctagctc catcagctcc tcttcttccc tgtctagcgc catctccagc     120
gcagcgtcca gcgcagtgcc gtccagctac agcagcattc gctctgtcat gtctagcagc     180
ggcatctcct cctccttctc ttcttcttcc ctgatgccga gcacgagctc tgatatcagc     240
attctgcagg cgcgcattta tgaaagcctg actagcagcc tgtggtctag cgctagctct     300
ctgctgtctt cttatctgga agaagttgaa gaatatgagg aagacgaaga a             351
```

<210> SEQ ID NO 10
<211> LENGTH: 117
<212> TYPE: PRT
<213> ORGANISM: Artificial Sequence
<220> FEATURE:
<223> OTHER INFORMATION: Synthetic

<400> SEQUENCE: 10

```
Met Ala Met Ser Asn Met Thr Tyr Asn Ser Val Phe Ser Ser Ala Tyr
1               5                   10                  15
Ser Met Leu Lys Ser Ser Ile Arg Ser Ser Ile Ser Ser Ser
            20                  25                  30
Ser Leu Ser Ser Ala Ile Ser Ser Ala Ala Ser Ser Ala Val Pro Ser
        35                  40                  45
Ser Tyr Ser Ser Ile Arg Ser Val Met Ser Ser Ser Gly Ile Ser Ser
    50                  55                  60
Ser Phe Ser Ser Ser Ser Leu Met Pro Ser Thr Ser Ser Asp Ile Ser
65                  70                  75                  80
Ile Leu Gln Ala Arg Ile Tyr Glu Ser Leu Thr Ser Ser Leu Trp Ser
                85                  90                  95
Ser Ala Ser Ser Leu Leu Ser Ser Tyr Leu Glu Glu Val Glu Glu Tyr
            100                 105                 110
Glu Glu Asp Glu Glu
        115
```

<210> SEQ ID NO 11
<211> LENGTH: 357
<212> TYPE: DNA
<213> ORGANISM: Artificial Sequence
<220> FEATURE:
<223> OTHER INFORMATION: Synthetic

<400> SEQUENCE: 11

```
atgcaccatc atcatcatca ttcttctggt gtagatctgg caatgtctaa catgacttac      60
aacaacgtat tcgaccacgc ttatgaaatg ctgaaagaaa acatccgtta tgatgatatc     120
cgcgatactg acgaccttca cgatgctatt cacatggctg cagataatgc agttccgcac     180
tactatgctg acatccgtag cgtaatggca agtgagggca ttgaccttga gtttgaagat     240
tccggtctga tgcctgacac caaggacgac atccgcatac tacaggctcg tatctatgaa     300
caattaacga ttgacctctg ggaagatgct gaggacttgc tgaacgaata cctcgag       357
```

<210> SEQ ID NO 12
<211> LENGTH: 119
<212> TYPE: PRT
<213> ORGANISM: Artificial Sequence
<220> FEATURE:

<223> OTHER INFORMATION: Synthetic

<400> SEQUENCE: 12

Met His His His His His Ser Ser Gly Val Asp Leu Ala Met Ser
1               5                   10                  15

Asn Met Thr Tyr Asn Asn Val Phe Asp His Ala Tyr Glu Met Leu Lys
            20                  25                  30

Glu Asn Ile Arg Tyr Asp Asp Ile Arg Asp Thr Asp Asp Leu His Asp
        35                  40                  45

Ala Ile His Met Ala Ala Asp Asn Ala Val Pro His Tyr Tyr Ala Asp
    50                  55                  60

Ile Arg Ser Val Met Ala Ser Glu Gly Ile Asp Leu Glu Phe Glu Asp
65                  70                  75                  80

Ser Gly Leu Met Pro Asp Thr Lys Asp Asp Ile Arg Ile Leu Gln Ala
                85                  90                  95

Arg Ile Tyr Glu Gln Leu Thr Ile Asp Leu Trp Glu Asp Ala Glu Asp
            100                 105                 110

Leu Leu Asn Glu Tyr Leu Glu
        115

<210> SEQ ID NO 13
<211> LENGTH: 321
<212> TYPE: DNA
<213> ORGANISM: Artificial Sequence
<220> FEATURE:
<223> OTHER INFORMATION: Synthetic

<400> SEQUENCE: 13
atggcaatgt ctaacatgac ttacaacaac gtattcgacc acgcttatga aatgctgaaa      60
gaaaacatcc gttatgatga tatccgcgat actgacgacc tcacgatgc tattcacatg      120 gctgcagata atgcagttcc gcactactat gctgacatcc gtagcgtaat ggcaagtgag      180
ggcattgacc ttgagtttga agattccggt ctgatgcctg acaccaagga cgacatccgc      240
atactacagg ctcgtatcta tgaacaatta acgattgacc tctgggaaga tgctgaggac      300
ttgctgaacg aatacctcga g                                                321

<210> SEQ ID NO 14
<211> LENGTH: 107
<212> TYPE: PRT
<213> ORGANISM: Artificial Sequence
<220> FEATURE:
<223> OTHER INFORMATION: Synthetic

<400> SEQUENCE: 14

Met Ala Met Ser Asn Met Thr Tyr Asn Asn Val Phe Asp His Ala Tyr
1               5                   10                  15

Glu Met Leu Lys Glu Asn Ile Arg Tyr Asp Asp Ile Arg Asp Thr Asp
            20                  25                  30

Asp Leu His Asp Ala Ile His Met Ala Ala Asp Asn Ala Val Pro His
        35                  40                  45

Tyr Tyr Ala Asp Ile Arg Ser Val Met Ala Ser Glu Gly Ile Asp Leu
    50                  55                  60

Glu Phe Glu Asp Ser Gly Leu Met Pro Asp Thr Lys Asp Asp Ile Arg
65                  70                  75                  80

Ile Leu Gln Ala Arg Ile Tyr Glu Gln Leu Thr Ile Asp Leu Trp Glu
                85                  90                  95

Asp Ala Glu Asp Leu Leu Asn Glu Tyr Leu Glu
            100                 105

<210> SEQ ID NO 15
<211> LENGTH: 143
<212> TYPE: PRT
<213> ORGANISM: Artificial Sequence
<220> FEATURE:
<223> OTHER INFORMATION: Synthetic

<400> SEQUENCE: 15

```
Met His His His His His Ser Ser Gly Val Asp Leu Ala Met Ser
1               5                   10                  15

Asn Met Thr Tyr Asn Asn Val Phe Asp His Ala Tyr Glu Met Leu Lys
            20                  25                  30

Glu Asn Ile Arg Tyr Asp Asp Ile Arg Asp Thr Asp Leu His Asp
        35                  40                  45

Ala Ile His Met Ala Ala Asp Asn Ala Val Pro His Tyr Tyr Ala Asp
    50                  55                  60

Ile Arg Ser Val Met Ala Ser Glu Gly Ile Asp Leu Glu Phe Glu Asp
65                  70                  75                  80

Ser Gly Leu Met Pro Asp Thr Lys Asp Asp Ile Arg Ile Leu Gln Ala
                85                  90                  95

Arg Ile Tyr Glu Gln Leu Thr Ile Asp Leu Trp Glu Asp Ala Glu Asp
            100                 105                 110

Leu Leu Asn Glu Tyr Leu Glu Glu Val Glu Glu Tyr Glu Glu Asp Glu
        115                 120                 125

Glu Gly Thr Glu Asn Leu Tyr Phe Gln Ser Asn Ile Cys Ser Gly
    130                 135                 140
```

<210> SEQ ID NO 16
<211> LENGTH: 141
<212> TYPE: PRT
<213> ORGANISM: Artificial Sequence
<220> FEATURE:
<223> OTHER INFORMATION: Synthetic

<400> SEQUENCE: 16

```
Met His His His His His Ser Ser Gly Val Asp Leu Met Ala Met
1               5                   10                  15

Ser Asn Met Thr Tyr Asn Asn Val Phe Asp His Ala Tyr Glu Met Leu
            20                  25                  30

Lys Glu Asn Ile Arg Tyr Asp Asp Ile Arg Asp Thr Asp Leu His
        35                  40                  45

Asp Ala Ile His Met Ala Ala Asp Asn Ala Val Pro His Tyr Tyr Ala
    50                  55                  60

Asp Ile Arg Ser Val Met Thr Ser Glu Gly Ile Asp Leu Glu Phe Glu
65                  70                  75                  80

Asp Ser Gly Leu Met Pro Asp Thr Lys Asp Asp Ile Arg Ile Leu Gln
                85                  90                  95

Ala Arg Ile Tyr Glu Gln Leu Thr Ile Asp Leu Trp Glu Asp Ala Glu
            100                 105                 110

Asp Leu Leu Asn Glu Tyr Leu Glu Glu Val Glu Glu Tyr Glu Glu Asp
        115                 120                 125

Glu Glu Gly Thr Glu Asn Leu Tyr Phe Gln Ser Asn Ala
    130                 135                 140
```

<210> SEQ ID NO 17
<211> LENGTH: 12
<212> TYPE: DNA
<213> ORGANISM: Artificial Sequence

```
<220> FEATURE:
<223> OTHER INFORMATION: Synthetic

<400> SEQUENCE: 17
atcgagggta gg                                                          12

<210> SEQ ID NO 18
<211> LENGTH: 4
<212> TYPE: PRT
<213> ORGANISM: Artificial Sequence
<220> FEATURE:
<223> OTHER INFORMATION: Synthetic

<400> SEQUENCE: 18

Ile Glu Gly Arg
1

<210> SEQ ID NO 19
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: n is a, c, g, or t

<400> SEQUENCE: 19
tacttccaat ccaatgcn                                                    18

<210> SEQ ID NO 20
<211> LENGTH: 19
<212> TYPE: DNA
<213> ORGANISM: Artificial Sequence
<220> FEATURE:
<223> OTHER INFORMATION: Synthetic

<400> SEQUENCE: 20
ttatccactt ccaatgtta                                                   19

<210> SEQ ID NO 21
<211> LENGTH: 19
<212> TYPE: DNA
<213> ORGANISM: Artificial Sequence
<220> FEATURE:
<223> OTHER INFORMATION: Synthetic

<400> SEQUENCE: 21
ttatccactt ccaatgcta                                                   19

<210> SEQ ID NO 22
<211> LENGTH: 348
<212> TYPE: DNA
<213> ORGANISM: Bacteriophage T7

<400> SEQUENCE: 22
gctatgtcta acatgactta caacaacgtt ttcgaccacg cttacgaaat gctgaaagaa      60
aacatccgtt atgatgacat ccgtgacact gatgacctgc acgatgctat tcacatggct     120
gccgataatg cagttccgca ctactacgct gacatcttta gcgtaatggc aagtgagggc     180
attgaccttg agttcgaaga ctctggtctg atgcctgaca ccaaggacgt aatccgcatc     240
ctgcaagcgc gtatctatga gcaattaacg attgacctct gggaagacgc agaagacttg     300
ctcaatgaat acttggagga agtcgaggag tacgaggagg atgaagag                  348
```

```
<210> SEQ ID NO 23
<211> LENGTH: 116
<212> TYPE: PRT
<213> ORGANISM: Bacteriophage T7

<400> SEQUENCE: 23

Ala Met Ser Asn Met Thr Tyr Asn Asn Val Phe Asp His Ala Tyr Glu
1               5                   10                  15

Met Leu Lys Glu Asn Ile Arg Tyr Asp Asp Ile Arg Asp Thr Asp Asp
            20                  25                  30

Leu His Asp Ala Ile His Met Ala Ala Asp Asn Ala Val Pro His Tyr
        35                  40                  45

Tyr Ala Asp Ile Phe Ser Val Met Ala Ser Glu Gly Ile Asp Leu Glu
    50                  55                  60

Phe Glu Asp Ser Gly Leu Met Pro Asp Thr Lys Asp Val Ile Arg Ile
65                  70                  75                  80

Leu Gln Ala Arg Ile Tyr Glu Gln Leu Thr Ile Asp Leu Trp Glu Asp
                85                  90                  95

Ala Glu Asp Leu Leu Asn Glu Tyr Leu Glu Glu Val Glu Glu Tyr Glu
            100                 105                 110

Glu Asp Glu Glu
        115
```

PROTEIN PURIFICATION TAGS AND USES THEREOF

CROSS REFERENCE TO RELATED APPLICATIONS

This application is a 371 of PCT/US09/52440 filed Jul. 31, 2009, which claims priority to U.S. Provisional Application 61/085,648 filed on Aug. 1, 2008, which is herein incorporated by reference in its entirety.

GOVERNMENT SUPPORT

This invention was made with government support under grant GM65330 awarded by the National Institutes of Health. The government has certain rights in the invention.

FIELD OF THE INVENTION

The present invention relates to fusion proteins. In particular, the present invention relates to protein tags for use in protein solubilization and purification.

BACKGROUND OF THE INVENTION

Due to its low cost, compatibility with automation and ease of scale-up, *E. coli* remains the most widely used host for high-throughput protein production (Hedren et al., Acta Cryst. 62 (2006) 1227-1231; Goulding and Perry, J. Structural Biol. 142 (2003) 133-143; Cabrita et al., BMC Biotechnology 6 (2006)). A major hurdle for heterologous protein production in *E. coli* is the formation of insoluble aggregates. This problem is commonly addressed through the use of fusion tags to enhance solubility (Waugh, TRENDS in Biotechnology 23 (2006) 316-320; Terpe, Appl. Microbiol Biotechnol 60 (2003) 523-533; Esposito and Chatterjee, Curr. Opin. Biotechnology, 17 (2006) 353-358). Comparative studies of the effectiveness of fusion tags have shown the maltose-binding protein (MBP) to be one of the best at solubilizing passenger proteins (Kapust and Waugh, Protein Science 8 (1999) 1668-1674; Hammarstrom et al., Potein Science 11 (2002) 313-321). The properties that make a fusion tag capable of enhancing solubility are not fully understood, although the acidity of the fusion tag is often correlated with this capability (Fox et al., FEBS Letters 537 (2003) 53-57; Su et al., J. Biotechnology 129 (2007) 373-382). Due to MBP's solubilizing capability and its affinity for amylose, which allow it to be used as an affinity handle, vectors containing MBP fusion tags have been developed for use in high-throughput cloning and expression (Donnelly et al., Protein Expr. Purif. 47 (2006) 446-454).

Although MBP is quite effective in solubilizing its passenger proteins during expression, a number of problems have been identified with its use. These problems can occur during purification and processing of the fusion. MBP fusions do not always bind to amylose resin and so a His tag is commonly added to facilitate affinity purification using a metal chelating resin (Pryor and Leiting, Protein Expr. Purif. 10 (1997) 309-319). Many proteins that are soluble when fused to MBP have been observed to precipitate when the MBP-fusion is cleaved (Donnelly et al., supra). Additionally, the incomplete removal of MBP from the passenger protein after cleavage of the fusion (Donnelly et al., supra) may interfere with downstream applications such as NMR or crystallization.

Thus, what is needed are improved fusion partners for solubilization and purification of proteins of interest.

SUMMARY OF THE INVENTION

The present invention relates to fusion proteins. In particular, the present invention relates to protein tags for use in protein solubilization and purification.

Throughout the specification and claims, where amino acid sequence positions numbers are given, such numbering is with regard to Ocr polypeptide as presented in SEQ ID NO:23.

In some embodiments, the present invention provides a composition comprising a variant ocr nucleic acid sequence, wherein the variant nucleic acid sequence encodes a monomeric Ocr protein. In some embodiments, the protein comprises variant amino acids that prevent dimerization. In some embodiments, the monomeric Ocr protein has altered amino acids at one or more positions (e.g., 50, 53, 54, 55, 56, 57, and 77). In some embodiments, the monomeric Ocr protein has F53R and V77D mutations. In some embodiments, the monomeric Ocr protein encoded by the nucleic acid has the amino acid sequence of SEQ ID NO:2. In some embodiments, the variant ocr nucleic acid sequence has the nucleic acid sequence of SEQ ID NO:1. In some embodiments, the variant ocr nucleic acid sequence is fused to a nucleic acid sequence encoding a protein of interest and the variant ocr nucleic acid sequence encodes a monomeric Ocr-protein of interest fusion protein. In some embodiments, the nucleic acid sequence is in an expression vector. In some embodiments, the expression vector is in a host cell (e.g., *E. coli*).

In other embodiments, the present invention provides an expression vector comprising a variant ocr nucleic acid sequence, wherein the variant nucleic acid sequence encodes a monomeric Ocr protein. In some embodiments, the variant ocr nucleic acid sequence is fused to a nucleic acid sequence encoding a protein of interest and the variant ocr nucleic acid sequence encodes a monomeric Ocr-protein of interest fusion protein.

In still further embodiments, the present invention provides a monomeric variant Ocr protein. In some embodiments, the protein comprises variant amino acids that prevent dimerization. In some embodiments, the monomeric Ocr protein has altered amino acids at one or more positions (e.g., 50, 53, 54, 55, 56, 57, and 77). In some embodiments, the monomeric Ocr protein has F53R and V77D mutations. In some embodiments, the monomeric Ocr protein encoded by the nucleic acid has the amino acid sequence of SEQ ID NO:2. In some embodiments, the monomeric Ocr protein is fused to a protein of interest.

The present invention further provides a method of expressing a protein of interest, comprising delivering an expression vector comprising an expression construct comprising a variant ocr nucleic acid sequence fused to a nucleic acid sequence encoding a protein of interest to a host cell; and expressing the expression construct under conditions such that a fusion protein comprising monomeric Ocr protein fused to a gene of interest is expressed. In some embodiments, the method further comprises the step of purifying the fusion protein (e.g., using DEAE chromatography). In some embodiments, the method further comprises the step of cleaving the fusion protein to generate a monomeric Ocr protein and a protein of interest (e.g., by contacting the fusion protein with tobacco etch virus (TEV) protease). In some embodiments, the monomeric Ocr protein has F53R and V77D mutations. In some embodiments, the monomeric Ocr protein has the amino acid sequence of SEQ ID NO:2. In some embodiments, the variant ocr nucleic acid sequence has the nucleic acid sequence of SEQ ID NO:1.

In some embodiments, the present invention provides a composition comprising a variant ocr nucleic acid sequence, wherein the variant nucleic acid sequence encodes a monomeric Ocr protein, and wherein the variant nucleic acid sequence encodes a monomeric Ocr protein with a pI that is more acidic than that of a monomeric Ocr protein with F53R and V77D mutations. In some embodiments, the monomeric Ocr protein with acidic pI comprises N4D, N9D, H13D, N21D, Y24E, R28D, H34D, H38D, M39D, N43D, H47D, Y48D, A50D, S54D, A57D, S68D, K75D, R79E, A83D, Q88E, I91D, and N102D mutations. In some embodiments, the variant nucleic acid sequence encodes a monomeric Ocr protein with a pI that is more basic than that of a monomeric Ocr protein with F53R and V77D mutations. In some embodiments, the monomeric Ocr protein with basic pI comprises D12N, H13R, E16R, M17K, E20Q, Y24R, D25N, D26N, D29N, D31R, D32N, D35N, M39K, M42N, Y48R, A50R, D51N, A57R, E59Q, D62H, L63R, E64Q, E66Q, D67H, D73H, D76H, E106Q, E107Q, E109Q, E110Q, E112Q, E113Q, D114N, E115Q, and E116Q mutations. In some embodiments, the variant nucleic acid sequence encodes a monomeric Ocr protein with a pI that is more uncharged than that of a monomeric Ocr protein with F53R and V77D mutations. In some embodiments, the monomeric Ocr protein with a pI that is more uncharged than that of a monomeric Ocr protein with F53R and V77D mutations comprises N9S, D12S, H13S, E16S, E20S, N21S, Y42S, D25S, D26S, R28S, D29S, T30S, D31S, D32S, H34S, D35S, H38S, M39S, D42S, N43S, H47S, Y48S, A50S, D51S, A57S, E59S, D62S, L63S, E64S, E66S, D67S, G69S, D73S, D76S, R79S, Q88S, I91S, D92S, E95S, D96S, E98S, D99S, N102S, and E103S mutations.

DESCRIPTION OF THE FIGURES

FIG. 3 shows the amino acid sequence of the synthetic Mocr as it appears in the pMCSG7 vector (SEQ ID NO:15).

FIG. 13 shows classification of amino acids in SEQ ID NO:2 by the risk level of substitution at this position to structural integrity. Underlined Amino acids present the lowest risk, those in double underline are medium risk and those in dotted underline present the highest risk of causing a structural alteration upon substitution.

Figure 1:
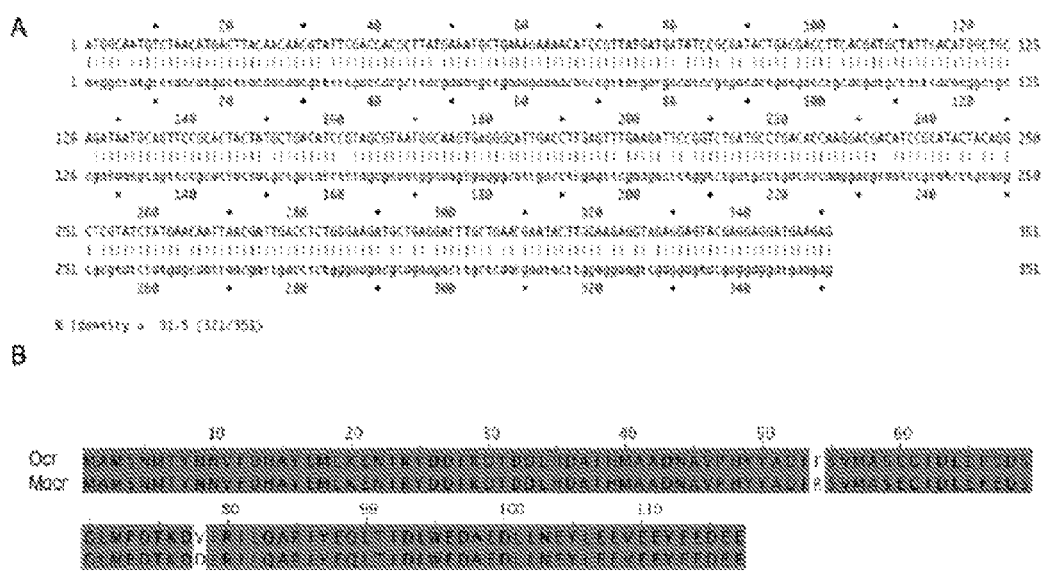
FIG. 1 shows nucleic acid and amino acid sequences of mocr and ocr genes. A. Strider alignment of the DNA sequence of the synthetic mocr gene (SEQ ID NO:3, top) and the native ocr gene (SEQ ID NO:23, bottom). B. Strider alignment of the Mocr amino acid sequence (SEQ ID NO:4, bottom) with the native Ocr amino acid sequence (SEQ ID NO:23, top).

FIG. 14 shows protein Mocr variants in which amino acid substitutions were made to result in an acidic (SEQ ID NO:6), basic (SEQ ID NO:8), or uncharged (serine-substituted, SEQ ID NO:9)) versions of the protein.

FIG. 15 shows an embodiment of the present invention in which a carboxyl-terminal unstructured region of the original Mocr protein is replaced with sequence encoding a rigid linker (SEQ ID NO:16).

FIG. 16 shows SEQ ID NOs 1-23.

DEFINITIONS

The term "gene" refers to a nucleic acid (e.g., DNA) sequence that comprises coding sequences necessary for the production of a polypeptide, RNA (e.g., rRNA, tRNA, etc.), or precursor. The polypeptide, RNA, or precursor can be encoded by a full length coding sequence or by any portion of the coding sequence so long as the desired activity or functional properties (e.g., ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments included when a gene is transcribed into heterogeneous nuclear RNA (hnRNA); introns may contain regulatory elements such as enhancers. Introns are removed or "spliced out" from the nuclear or primary transcript; introns therefore are generally absent in the messenger RNA (mRNA) transcript. The mRNA functions during translation to specify the sequence or order of amino acids in a nascent polypeptide. Variations (e.g., mutations, SNPS, insertions, deletions) in transcribed portions of genes are reflected in, and can generally be detected in, corresponding portions of the produced RNAs (e.g., hnRNAs, mRNAs, rRNAs, tRNAs).

Where the phrase "amino acid sequence" is recited herein to refer to an amino acid sequence of a peptide or protein molecule, amino acid sequence and like terms, such as polypeptide or protein are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. In this case, the DNA sequence thus codes for the amino acid sequence.

DNA and RNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; magnetic beads; enzymes; colorimetric labels; plastic beads; and fluorescent dyes (e.g., fluorescein dyes, rhodamine dyes, BODIPY, and Cy3 or Cy5) alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

As used herein, the term "sample" is used in its broadest sense. In one sense, it is meant to include cells (e.g., human, bacterial, yeast, and fungi), an organism, a specimen or culture obtained from any source, as well as biological and environmental samples. Biological samples may be obtained from animals (including humans) and refers to a biological material or compositions found therein, including, but not limited to, bone marrow, blood, serum, platelet, plasma, interstitial fluid, urine, cerebrospinal fluid, nucleic acid, DNA, tissue, and purified or filtered forms thereof. Environmental samples include environmental material such as surface matter, soil, water, crystals and industrial samples. Such examples are not however to be construed as limiting the sample types applicable to the present invention.

As used herein, the term "organism" refers to any entity from which total genomic DNA and/or RNA can be derived. For example, organisms may be subjects, strains, isolates, or species. In some embodiments, a subject, strain, isolate or species may be selected from humans, bacteria, viruses, yeast, algae, fungi, animals and plants.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

The following terms are used to describe the sequence relationships between two or more polynucleotides: "reference sequence," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, Adv. Appl. Math. 2: 482 (1981)] by the homology alignment algorithm of Needleman and Wunsch [Needleman and Wunsch, J. Mol. Biol. 48:443 (1970)], by the search for similarity method of Pearson and Lipman [Pearson and Lipman, Proc. Natl. Acad. Sci. (U.S.A.) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

As applied to polynucleotides, the term "substantial identity" denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a splice variant of the full-length sequences.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As used herein, the term "recombinant DNA molecule" as used herein refers to a DNA molecule that is comprised of segments of DNA joined together by means of molecular biological techniques.

The term "test compound" refers to any chemical entity, pharmaceutical, drug, and the like that are tested in an assay (e.g., a drug screening assay) for any desired activity (e.g., including but not limited to, the ability to treat or prevent a disease, illness, sickness, or disorder of bodily function, or otherwise alter the physiological or cellular status of a sample). Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acids encoding a polypeptide include, by way of example, such nucleic acid in cells ordinarily expressing the polypeptide where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (e.g., 10 nucleotides, 11, . . . , 20, . . . ).

As used herein, the term "purified" or "to purify" refers to the removal of contaminants from a sample. As used herein, the term "purified" refers to molecules (e.g., nucleic or amino acid sequences) that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

The term "signal" as used herein refers to any detectable effect, such as would be caused or provided by a label or an assay reaction.

As used herein, the term "container" is used in its broadest sense, and includes any material useful for holding a sample or organism. A container need not be completely enclosed. Containers include tubes (e.g., eppendorf or conical tubes), plates, wells, microtiter plate wells, or any material capable of separating one sample from another (e.g., a microfluidic channel or engraved space on a solid surface). Such examples are not however to be construed as limiting the containers applicable to the present invention.

As used herein, the term "kit" refers to any delivery system for delivering materials. In the context of reaction assays, such delivery systems include systems that allow for the storage, transport, or delivery of reagents (e.g., cloning vectors, protein controls, enzymes, etc. in the appropriate containers) and/or supporting materials (e.g., buffers, written instructions for performing cloning and expression etc.) from one location to another. For example, kits include one or more enclosures (e.g., boxes) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain a microarray for use in an assay, while a second container contains oligonucleotides. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "passenger protein" refers to any protein that is encoded by a nucleic acid sequence adjacent to a nucleotide sequence encoding a protein tag (e.g., a protein tag of some embodiments of the present invention, e.g., a Mocr protein or Mocr variant). Upon expression, a passenger protein and the protein tag comprise the same polypeptide molecule, although there may be intervening amino acid sequence between them (e.g., linker region, protease recognition site(s), etc.) A protein tag and passenger protein may be associated in any order. For example, where listed in order from amino-terminal to carboxy-terminal, the order of a protein tag and a passenger protein may be:

Protein tag—passenger protein;
Passenger protein—protein tag; or
Protein tag (partial or complete)—passenger protein—protein tag (partial or complete)

Other arrangements are contemplated, including but not limited to tandem repeats of protein tags and/or passenger proteins, such repeats being either intervening (e.g., ABABAB where A is a protein tag and B is a passenger protein) or repetitive (e.g., AABBAABB). In some embodiments, the arrangement is protein tag-passenger protein. The term "passenger protein" may be used interchangeably with "target protein".

As used herein, the term "fusion protein" refers to a polypeptide comprising a protein tag and a passenger protein, regardless of their relative location within the polypeptide.

DETAILED DESCRIPTION OF THE INVENTION

The present invention relates to fusion proteins. In particular, the present invention relates to protein tags for use in protein solubilization and purification.

Limited solubility is one of the challenges in production of recombinant protein. Protein fusion partners are commonly used to solve solubility problems, and MBP is one of the most successful solubilizing partners for bacterially expressed proteins (Kapust and Waugh, Protein Science 8 (1999) 1668-1674; Hammarstrom et al., Protein Science 11 (2002) 313-321). Although an excellent solubilizer, MBP is large (42 kDa) and may interfere with activity assays of the passenger protein. Some passengers interfere with the ability of MBP to bind amylose resin, and some proteins fall out of solution when MBP is removed from the fusion. It can also be difficult to purify the passenger protein away from MBP after the fusion is cleaved.

Experiments conducted during the course of development of embodiments of the present invention yielded a novel fusion tag (e.g., monomeric forms of the Ocr protein from bacteriophage T7) with solubilizing activity when used as a fusion tag. The novel protein tag is smaller than MBP and thus interferes less with downstream applications. It is also less likely to need to be removed from the purified fusion protein. In some embodiments, vectors containing this fusion tag are compatible with high-throughput cloning and expression processes.

Preferred fusion tags also function as affinity tags, that is, they may be used for purification of the passenger protein. The most commonly used affinity tag is the $His_6$ tag. This tag binds to immobilized transition metals and is commonly used to purify the protein of interest from the cell lysate. MBP is also an affinity tag. It can be bound to amylose resin. The efficiency of this binding interaction may be reduced by the addition of a passenger protein to the MBP and so a $His_6$ tag is frequently added to MBP fusions. In many cases this allows for high levels of purity to be attained because two affinity steps are available. Mocr protein can also be used as a purification handle with performance similar to affinity tags such as $His_6$. The tag can be cleaved from its passenger protein using a protease (e.g., TEV protease) and purified from the target protein by metal affinity, DEAE-cellulose or size exclusion chromatography. Uncleaved fusion protein may be fully active and in some cases may be compatible with assays of target protein function. Formation of dimers and receptor binding by the P domain of the MNV capsid protein and its ability to compete with native MNV in infectivity assays was not hindered by the presence of the Mocr fusion tag. Mocr is thus a useful fusion tag.

Numerous fusion proteins have been described but none is universally successful in solubilizing passenger proteins. Comparative studies have found wide variations in the performance of commonly used fusion tags (Kapust and Waugh, supra; Hammarstrom et al., supra). The properties that give a fusion tag solubilizing activity are not understood. In a recent report of two new fusion tags, E. coli protein Skp was thought to function through chaperone activity, but the mechanism for bacteriophage T7 protein kinase was not clear (Chatterjee and Esposito, Protein Expr. Purif. 46 (2006) 122-129). Data for mutant forms of MBP are also consistent with a chaperone-like mechanism for solubilizing passenger proteins (Nallamsetty and Waugh, Biochem. Biophys. Res. Commun. 364 (2007) 639-644). Another recent report attributed solubilizing activity to the acidity or charge of the fusion tag, E. coli protein Msb (Su et al., J. Biotechnology 129 (2007) 373-382), and there have been previous suggestions that this may be an important property of solubilizing fusion tags (Fox et al., FEBS Letters 537 (2003) 53-57). Wilkinson and Harrison developed a statistical model for predicting protein solubility in bacteria (Wilkinson and Harrison, Bio/Technol. 9 (1991) 443-448). A simplified version of this model, based on approximate charge average and turn-forming residue content, was developed as a predictor of suitable fusion proteins and used to identify the N-utilization substance A (NusA) protein (Davis et al., Biotechnol. Bioeng. 65 (1999) 382-388). NusA was predicted to have a 95% probability of solubility and then demonstrated to have solubilizing activity as a fusion tag. This model predicts Mocr to have a 97% probability of solubility and it also displays solubilizing activity.

The present invention is not limited to a particular mechanism. Indeed, an understanding of the mechanism is not necessary to practice the present invention. Nonetheless, although the mechanism of solubility enhancement by the Mocr protein is not known, its effectiveness suggests that acidity and/or charge may be an important factor. Mocr has an acidic pI and high charge, in common with other documented solubilizing fusion tags. For example, MBP, NusA, Msb and the bacteriophage T7 protein kinase also have acidic pIs. Although acidity appears to be an important parameter in solubility it is not the only factor. One mechanism of Mocr action may be its ability to reduce the aggregation of the passenger protein through Mocr's high charge. The addition of charged acidic tails to aggregation-prone proteins has been shown to have this effect (Zhang et al., Protein Expr. Purif. 36 (2004) 207-216). Charge repulsion between the acidic tails is thought to disrupt aggregation of the passenger protein. Such a charge-repulsion effect may be partially responsible for the solubility observed using the Mocr protein fusion. The Mocr protein has the additional advantage of being a stable, well-structured protein, unlike the acidic tails, which are most likely unstructured.

Although the Mocr fusion tag may be efficiently removed from the passenger protein, for some applications it may be preferable to leave the fusion intact. One such application is NMR analysis. As cloned in pMCSG7, the Mocr fusion protein adds 16.7 kDa to the passenger protein or peptide. MBP, as it is cloned into the pMCSG9 vector, adds 43.6 kDa to the passenger protein or peptide. In a uniformly labeled protein for use in NMR experiments, the additional mass of the MBP would greatly complicate the analysis and would require removal. A need to remove the fusion tag introduces a variety of complications and led to the development of smaller fusions partners such as GB1 (Huth et al., Protein Science 6 (1997) 2359-2364; Koenig et al., J. of Biomolecular NMR 26 (2003) 193-202) that do not require removal before spectroscopic analysis. Although larger than GB1, Mocr's size is consistent with the Domain I of E. coli initiation factor 2 (IF2, 17.4 kDa) that has also been proposed as a solubility fusion tag for use in NMR applications (Sorenson et al., Protein Expr. Purif. 32 (2003) 252-259).

Given the small size and compactness of the Mocr structure, it may be possible to crystallize the passenger protein while still fused to the Mocr protein. This has not been reported with larger fusion tags, such as GST and MBP, unless the passenger protein was very small, less than 115 amino acids (Smyth et al., Protein Science 12 (2003) 1313-1322).

In the crystal structure of Ocr protein, only residues 5-110 were ordered, of a total of 117 amino acids. During experiments conducted during the course of development of embodiments of the present invention, the pMCSG backbone included no additional linker between the Mocr and the TEV cleavage site because the disorder of the last seven amino acids of Mocr allow for protease access to the cleavage site. In a number of different Mocr fusions, complete cleavage of the fusion with TEV protease was observed. The four residues that are disorded at the Ocr amino terminus also provide an unstructured linker region to facilitate accessibility for TEV or other protease cleavage in a carboxyl fusion of Mocr.

Inclusion body formation in E. coli displays significant similarity to amyloid plaque formation (Carrio et al., J. Mol. Biol. 347 (2005) 1025-1037). Since aggregation of target protein may be driven by surface hydrophobicity as in plaque formation (Carrio et al., supra), a strategy to reduce this effect is the introduction of less polar solvents, such as ethanol, into lysis buffers. This would be analogous to work with amyloid-forming peptides for which addition of organic solvents such as ethanol (10%) and DMSO (5%) has the effect of disaggregating protein and stabilizing monomers (Sabate and J. Estelrich, Disaggregating effects of ethanol at low concentration on beta-poly-L-lysines, Int. J. of Biol. Macromol. 32 (2003) 10-16). Organic solvents may reduce aggregation but they may have a negative effect on overall protein product solubility. Ocr exhibits solubility in 95% ethanol (Mark and Studier, J. Biol. Chem. 256 (1981) 2573-2578). Thus, Mocr is contemplated to be soluble in a less polar solvent at the relatively low concentrations at which disaggregation has been observed for amyloid forming peptides, possibly stabilizing a passenger protein as a monomer in the soluble fraction of the lysate.

I. Mocr

As described above, embodiments of the present invention provide monomeric Ocr (Mocr) proteins and nucleic acids encoding Mocr for use in generating fusion proteins.

A. mocr Polynucleotides

As described above, experiments conducted during the course of development resulted in the generation of nucleic acids encoding Mocr proteins. The present invention is not limited to a particular mocr nucleic acid sequence. Any nucleic acid sequence that encodes a monomeric Mocr protein suitable for use in generating protein fusions for expression and purification is contemplated by the present invention. Exemplary nucleic acids encode the Mocr protein of SEQ ID NO: 2 (e.g., SEQ ID NO:1). In some embodiments, the present invention provides polynucleotide sequences that are capable of hybridizing to SEQ ID NO:1 under conditions of low to high stringency as long as the polynucleotide sequence capable of hybridizing encodes a protein that retains the monomeric state of Mocr. In some embodiments, the protein is 70% homologous to Mocr of SEQ ID NO:2, preferably 80% homologous to Mocr of SEQ ID NO:2, more preferably 90% homologous to Mocr of SEQ ID NO:2, and most preferably 95% homologous to Mocr of SEQ ID NO:2.

In preferred embodiments, hybridization conditions are based on the melting temperature (Tm) of the nucleic acid binding complex and confer a defined "stringency" as explained above (See e.g., Wahl, et al., Meth. Enzymol., 152:399-407 [1987], herein incorporated by reference in its entirety).

In some embodiments of the present invention, the nucleotide sequences of the present invention may be engineered in order to alter a mocr coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In other embodiments of the present invention, variants of the disclosed mocr sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., monomeric or dimeric state) for such purposes as altering (e.g., decreasing) the dimerization ability of Mocr. Such modified peptides are considered functional equivalents of peptides having an activity of Mocr as defined herein. A modified peptide can be produced in which the nucleotide sequence encoding the polypeptide has been altered, such as by substitution, deletion, or addition. In particularly preferred embodiments, these modifications do not significantly reduce the synthetic activity of the modified Mocr. In other words, construct "X" can be evaluated in order to determine whether it is a member of the genus of modified or variant Mocr's of the present invention as defined functionally, rather than structurally.

Moreover, as described above, variant forms of Mocr are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of Mocr disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a mocr coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

B. Mocr Polypeptides

In other embodiments, the present invention provides mocr polynucleotide sequences that encode Mocr polypeptides (e.g., SEQ ID NO:2). Other embodiments of the present invention provide fragments, fusion proteins or functional equivalents of these Mocr proteins. In still other embodiments of the present invention, nucleic acid sequences corresponding to Mocr variants, homologs, and mutants may be used to generate recombinant DNA molecules that direct the expression of the Mocr variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NO:1 that encode substantially the same or a functionally equivalent amino acid sequence, may be used to clone and express Mocr or Mocr fusion proteins. In general, such polynucleotide sequences hybridize to SEQ ID NO:1 under conditions of high to medium stringency as described above. As will be understood by those of skill in the art, it may be advantageous to produce Mocr-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of Mocr expression or to produce recombinant RNA transcripts having desirable properties, such as a longer half-life, than transcripts produced from naturally occurring sequence.

Still other embodiments of the present invention provide mutant or variant forms of Mocr (i.e., muteins). As described above, preferred Mocr variants are those that result in a monomeric form of the protein. Exemplary mutations include, but are not limited to, F53R and V77D. The present invention is not limited to the mutations described herein. Additional mutations that result in a monomeric Mocr protein are also contemplated including, but not limited to, F53K and V77E. In addition, substitution of amino acids with polar side chains or charged amino acids for amino acids in the hole region (50 and 54-57) is also contemplated to disrupt dimerization and generate a monomeric Mocr protein.

Figure 9:
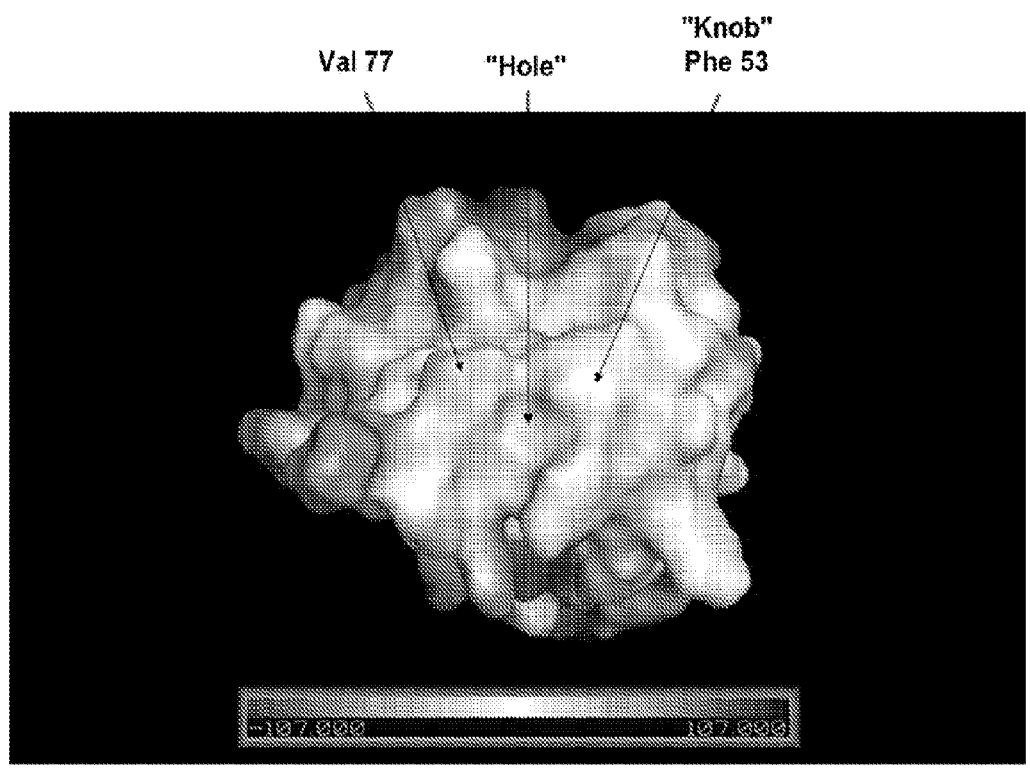
FIG. 9 shows Ocr's protein contact potential around Helix 4.

In particular, the Ocr dimer is formed through the interaction of a relatively small hydrophobic surface on one protein subunit with the same surface on a second subunit. The hydrophobic surface is formed by side chains of amino acids in or near helix 4 (Tyr 48 to Ala 57), based on the reported three-dimensional structure of Ocr (Walkinshaw et al., Mol. Cell 9 (2002) 187-194; herein incorporated by reference in its entirety). A representation of the hydrophobic character of this surface is shown in FIG. 9. The program PyMOL (DeLano, W. L. The PyMOL Molecular Graphics System (2007) DeLano Scientific LLC, Palo Alto, Calif., USA was used to estimate the electrostatic potential for the surface in the region of helix 4. Surfaces shaded red have negative charge potential, those shaded blue have positive charge potential and those shaded white are non-polar areas with net neutral charge potential. The non-polar white areas are created by the side chains of hydrophobic amino acids. A "knob" formed by the protruding Phe 53 is adjacent to a "hole" formed by Ala 50, Ser 54, Met 56, and Ala 57. To form the dimer, the "knob" of one subunit fits into the "hole" of the other subunit. Additional dimer contacts are formed by the side chains of Val 77 in the two monomers. Hydrophobic surface patches like the one shown in FIG. 9 are typical of protein-protein interaction sites, which also have complementary shapes. The Ocr dimer interface between complementary hydrophobic surfaces has no hydrogen bonds or ionic contacts.

Figure 10:
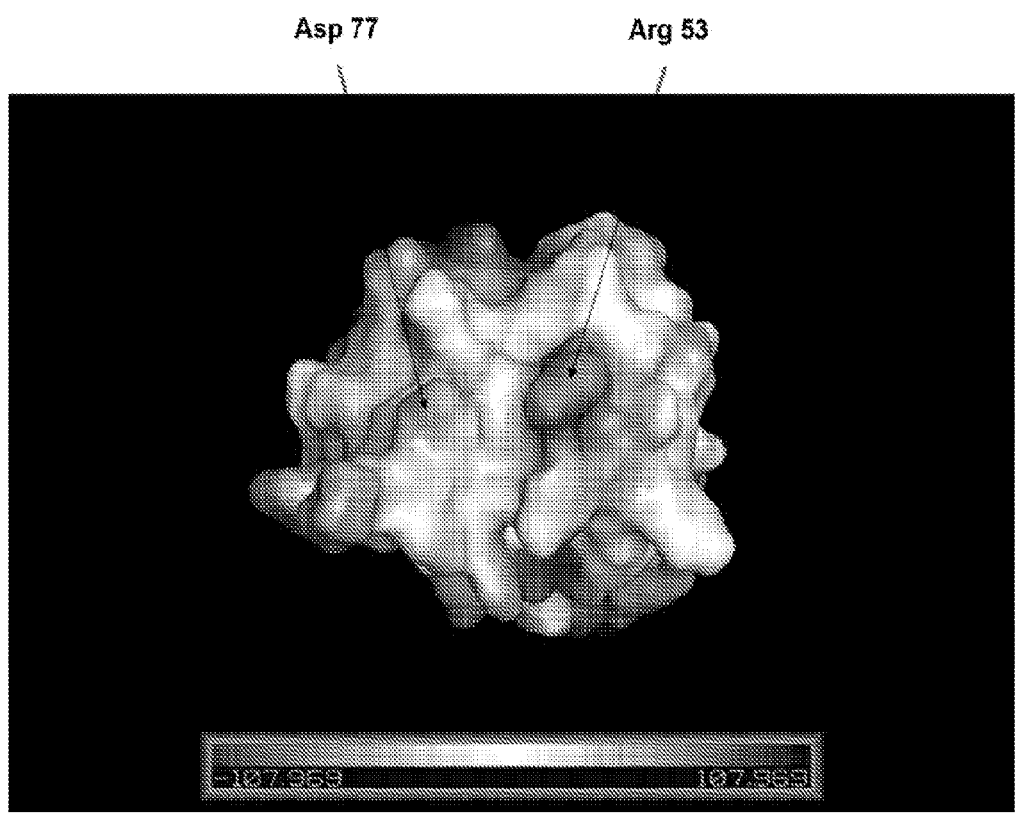
FIG. 10 shows Mocr's protein contact potential around Helix 4.

In some embodiments, to disrupt dimerization, mutations are made that alter the character of the surface shown in FIG. 9 by diminishing its hydrophobicity, reducing its shape complementarity, and introducing electrostatic repulsion. For example, as described above, Phe 53 was changed to an Arg and Val 77 was changed to an Asp. The electrostatic surface potential of the designed mutant form is shown in FIG. 10. As can be seen in the figure, the hydrophobic patch has been drastically reduced in size. The "hole" is partially covered by the Arg side chain at position 53. This charged amino acid is unable to interact with the hydrophobic "hole" on another subunit. The charged Asp side chain at position 77 abolishes the possibility for van der Waals contacts and instead causes charge repulsion if two Ocr monomers are brought together.

Figure 11:
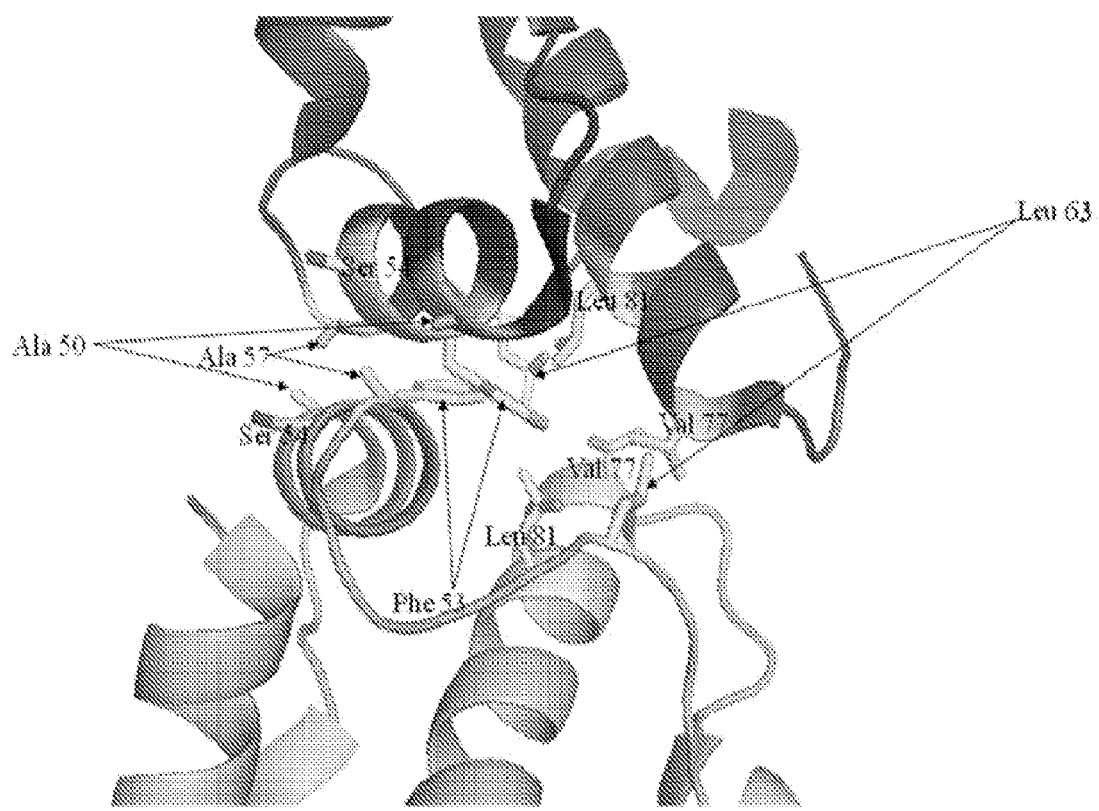
FIG. 11 shows elect amino acids at the Ocr dimer interface surface.

FIG. 11 shows some of the amino acids at the subunit interface of an Ocr dimer. All these hydrophobic amino acids contribute to the hydrophobic surface that forms the dimer. In some embodiments, any or all of these amino acids are substituted with a charged or polar amino acid in order to reduce the surface hydrophobicity and lead to the creation of a stable monomeric form of the protein. For example, the small side chains of both Ala 50 and Ala 57 are oriented towards the outer surface of helix 4 and contribute to the "hole" at the dimer interface surface. If these alanines were substituted with charged amino acids (for example Asp, Glu, Lys or Arg) or polar amino acids (for example Asn, Gln, Thr, etc.), the surface of helix 4 would not present a hydrophobic "hole" and would interact better with the polar solvent. The Ser at position 54 is polar but its side chain is small. This amino acid can be substituted with a polar amino acid with a longer side chain such as Gln or Asn, or it can be substituted with a charged amino acid such as Arg or Lys. Alternative changes can also be made to the contact points at Phe 53 and Val 77. Substitution with the charged or polar amino acids at these positions would have had a similar effect in reducing the hydrophobic surface area. Additional amino acids that participate in the formation of the hydrophobic surface are Leu 63 and Leu 81. Substitution of either or both of these amino acids with any of the charged or polar amino acids reduces the hydrophobic surface and promotes greater solvent accessibility. Any substitution that accomplishes this effect stabilizes the monomer form of the protein. Thus, any of the above described substitutions can be used to generate monomeric forms of Mocr.

Figure 12:
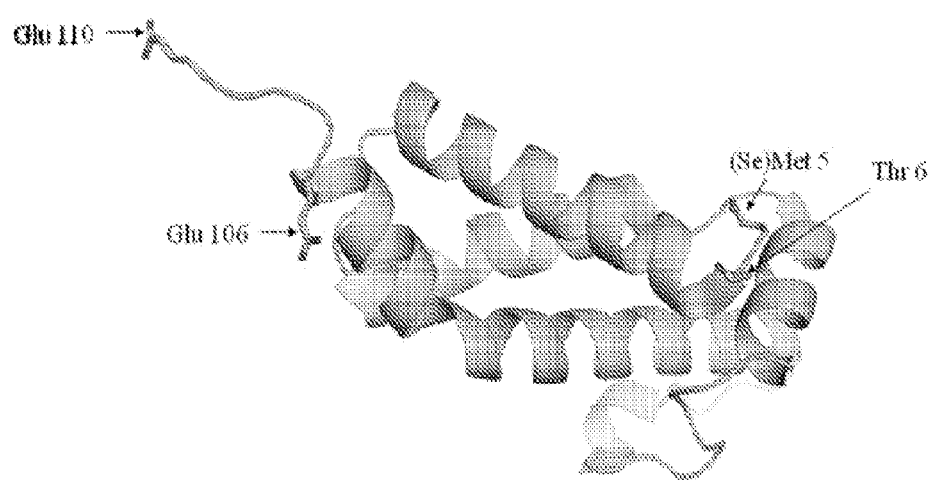
FIG. 12 shows amino acids visible in the electron density map from X-ray crystallography of Ocr and potential ends of a truncated molecule.

In some embodiments, truncated Mocr proteins are utilized. For example, FIG. 12 shows the overall Ocr structure and the locations of chain termini. The first four amino acids at the amino terminus and the last six amino acids at the carboxyl terminus (residues 113-116) were not visible in the electron density map of the Ocr crystal structure, suggesting that these amino acids are disordered. It is thus possible to remove either or both sets of these amino acids without compromising the structural integrity of the protein. Secondary structures in the protein core begin at residue Thr 6 (helix 1) and end at residue Glu 106 (helix 7). Truncation of all the amino acids beyond these residues is contemplated to result in a functional protein. Any combination of amino termini of amino acids 1 through 5 with carboxyl termini of amino acids 107 through 116 are contemplated to function as protein solubilization and purification tags.

In other embodiments, additional mutations that do not affect the folding or function of the protein are made in regions other than those involved in dimerization. Numerous sites in the protein can be mutated without disrupting the secondary or tertiary structure. Each residue was designated as external or fully or partially buried. For residues found to be fully or partially buried, the larger and more non-polar the residue is, the more likely it is to affect the stability of the tertiary structure. It was also evaluated whether the position is in an ordered or disordered portion of the protein or if the residues participate in secondary structure. For example, prolines at the ends of helices are considered to function as helix breakers.

Using these criteria, the amino acid positions were designated into three groups defined by the estimated risk of substitution to the structural integrity of the protein (FIG. 13). Amino acid positions shown in underline present the lowest estimated risk for structural alteration of the protein upon substitution. Since these are primarily on the surface of alpha helices or in loop regions, they can be substituted with charged or polar amino acids, with the exception of proline, without disrupting the secondary or tertiary structure of Ocr. Relative to amino acids shown in underline, those shown in double underline are more sensitive to the size of the substituted side-chain or may show a greater sensitivity to charge changes. The amino acids shown in dotted underline have a role in supporting the protein structure. These positions are likely to display significant sensitivity to substitutions that change the charge or polarity of the wild-type amino acid.

In some embodiments, mutations to Mocr-encoding nucleic acid sequences were made to result in Mocr variants with altered pI values (e.g., Example 2). The mechanism of solubilization by a fusion partner and the properties that give rise to this ability are multifold. While the present invention is not limited to any particular mechanism, and an understanding of the mechanism is not necessary to practice the present invention, it has been proposed that acidity of the fusion protein is a contributing factor for solubilization activity. In contrast, it has also been reported that the addition of a basic tag, Z-basic protein domain, can increase soluble protein over what is obtained with a His$_6$ tag (Hedhammar, et. al., J. Biotechnology 119 (2005) 133-146; herein incorporated by reference in its entirety). Therefore, while the present invention is not limited to any particular mechanism, and an understanding of the mechanism is not necessary to practice the present invention, it is contemplated that charge rather than pI is an important factor for solubilization activity.

Some Mocr constructs have a greater ability to be crystallized as a fusion protein (e.g., Example 3). While the present invention is not limited to any particular mechanism, and an understanding of the mechanism is not necessary to practice the present invention, it is contemplated that it may be necessary to have a rigid linker between the fusion partners for optimal crystallization of fusion proteins (Kobe, et. al., Proc. Natl. Acad. Sci. 96 (1999) 4319-4324; herein incorporated by reference in its entirety). While the present invention is not limited to any particular mechanism, and an understanding of the mechanism is not necessary to practice the present invention, it is contemplated that such a linker acts to reduce the possible conformations of the fusion protein, which in turn facilitates its ability to crystallize. Therefore, in some embodiments, additions, deletions, or substitutions are made to Mocr-encoding nucleic acid sequences to alter the linker region between the Mocr protein tag and the passenger protein.

It is possible to modify the structure of a peptide having an activity of Mocr for such purposes as enhancing solubility or stability (e.g., ex vivo shelf life, and/or resistance to proteolytic degradation in vivo). Such modified peptides are considered functional equivalents of peptides having an activity of the subject Mocr proteins as defined herein. A modified peptide can be produced in which the amino acid sequence has been altered, such as by amino acid substitution, deletion, or addition.

Moreover, as described above, variant forms (e.g., mutants or polymorphic sequences) of the subject Mocr proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present Mocr proteins, as well as truncation mutants, and is especially useful for identifying potential variant sequences (i.e., mutants or polymorphic sequences) that are functional in solubilizing and purifying passenger proteins. Therefore, in some embodiments of the present invention, Mocr variants are engineered by the present method to provide altered (e.g., decreased) dimerization.

Still other embodiments of the present invention provide Mocr variants that have intracellular half-lives dramatically different than the corresponding wild-type protein. For example, the altered protein can be rendered either more stable or less stable to proteolytic degradation or other cellular processes that result in destruction of or otherwise inactivate Mocr. Such variants, and the genes which encode them, can be utilized to alter the location of Mocr expression by modulating the half-life of the protein. For instance, a short half-life can give rise to more transient Mocr biological effects and, when part of an inducible expression system, can allow tighter control of Mocr fusion protein levels within the cell. As above, such proteins, and particularly their recombinant nucleic acid constructs, can be used in gene therapy protocols.

In a preferred embodiment of the present invention, the combinatorial Mocr library is produced by way of a degenerate library of genes encoding a library of polypeptides which each include at least a portion of potential Mocr protein sequences. For example, a mixture of synthetic oligonucleotides can be enzymatically ligated into gene sequences such that the degenerate set of potential Mocr sequences are expressible as individual polypeptides, or alternatively, as a set of larger fusion proteins (e.g., for phage display) containing the set of Mocr sequences therein.

There are many ways by which the library of potential Mocr homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential Mocr sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., Annu Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; as well as U.S. Pat. Nos. 5,223,409, 5,198,346, and 5,096,815; each of which is incorporated herein by reference).

It is contemplated that the Mocr nucleic acids (e.g., SEQ ID NO:1, and fragments and variants thereof) can be utilized as starting nucleic acids for directed evolution. In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1:17-24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for Mocr activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370:324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of Mocr homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

II. Constructs

In some embodiments, the present invention provides expression constructs for expressing Mocr fusion proteins with a protein of interest (e.g., passenger protein). In some embodiments, constructs comprise an expression vector for expression in a bacterial or eukaryotic cell. In some embodiments, expression vectors comprise promoters, nucleic acid sequences encoding mocr fused to or fusable to a gene of interest, with or without a linker sequence, and all other components necessary, sufficient, or useful for expression in a host cell.

A. Linking Sequence

A DNA fragment coding for a predetermined peptide may be employed to link the DNA fragments coding for the Mocr protein and protein molecule of interest. The predetermined peptide is preferably one which is recognized and cleaved by a proteolytic agent such that it cuts the hybrid polypeptide at or near the protein molecule without interfering with the biological activity of the protein molecule of interest. One such DNA fragment coding for a predetermined polypeptide is described in Nagai et al., Nature, Vol. 309., pp. 810-812 (1984), the disclosure of which is hereby incorporated by reference. This DNA fragment has the oligonucleotide sequence: ATCGAGGGTAGG (SEQ ID NO:17) and codes for the polypeptide Ile-Glu-Gly-Arg (SEQ ID NO:18). This polypeptide is cleaved at the carboxy side of the arginine residue using blood coagulation factor Xa. The present invention is not limited to any particular protease cleavage site. Indeed, in some embodiments, other protease cleavage recognition sites are included or substituted (e.g., protease cleavage recognition sites for Tobacco Etch Virus (TEV), proteinase K, enterokinase, thermolysin, thrombin, HRV 3C protease). As noted above, the linking sequence, in addition to providing a convenient cut site, may also serve as a polylinker, i.e. by providing multiple restriction sites to facilitate fusion of the DNA fragments coding for the target and binding proteins, and/or as a spacing means which separates the target and binding protein which, for example, allows access by the proteolytic agent to cleave the hybrid polypeptide.

B. Protein Molecule

The present invention may be beneficially employed to produce substantially any prokaryotic or eukaryotic, simple or conjugated protein that can be expressed by a vector in a transformed host cell. Such proteins include enzymes including endonucleases, methylases, oxidoreductases, transferases, hydrolases, lyases, isomerases or ligases.

The present invention also contemplates the production of storage proteins, such as ferritin or ovalbumin or transport proteins, such as hemoglobin, serum albumin or ceruloplasmin. Also included are the types of proteins that function in contractile and motile systems, for instance, actin and myosin.

The present invention also contemplates the production of antigens or antigenic determinants which can be used in the preparation of vaccines or diagnostic reagents.

The present invention also contemplates the production of proteins that serve a protective or defense function, such as the blood proteins thrombin and fibrinogen. Other protective proteins include the binding proteins, such as antibodies or immunoglobulins that bind to and thus neutralize antigens.

The protein produced by the present invention also may encompass various hormones such as Human Growth Hormone, somatostatin, prolactin, estrone, progesterone, melanocyte, thyrotropin, calcitonin, gonadotropin and insulin. Other such hormones include those that that have been identified as being involved in the immune system, such as interleukin 1, interleukin 2, colony stimulating factor, macrophage-activating factor and interferon.

The present invention is also applicable to the production of toxic proteins, such as ricin from castor bean or grossypin from cotton linseed.

Proteins that serve as structural elements may also be produced by the present invention; such proteins include the fibrous proteins collagen, elastin and alpha-keratin. Other structural proteins include glyco-proteins, virus-proteins and muco-proteins.

In addition to the above-noted naturally occurring proteins, the present invention may be employed to produce synthetic proteins defined generally as any sequences of amino acids not occurring in nature.

Genes coding for the various types of protein molecules identified above may be obtained from a variety of prokaryotic or eukaryotic sources, such as plant or animal cells or bacteria cells. The genes can be isolated from the chromosome material of these cells or from plasmids of prokaryotic cells by employing standard, well-known techniques. A variety of naturally occurring and synthetic plasmids having genes encoding many different protein molecules are now commercially available from a variety of sources. The desired DNA also can be produced from mRNA by using the enzyme reverse transcriptase. This enzyme permits the synthesis of DNA from an RNA template.

In some embodiments, it is contemplated that modified or unnatural forms of amino acids are incorporated into the expressed protein (e.g., radiolabeled amino acids, fluorescently labeled amino acids, amino acid derivatives, amino acid analogs).

The present invention is not limited to exemplary types of proteins listed supra, nor to specific proteins listed in Example 1.

C. Preparation of DNA Fusion and Expression Vectors

Various procedures and materials for preparing recombinant vectors; transforming host cells with the vectors; replicating the vector and expressing polypeptides and proteins; are known by the skilled artisan and are discussed generally in Maniatis et al., Molecular Cloning: A Laboratory Manual, CSH 1982, the disclosure of which is hereby incorporated by reference.

In practicing the present invention, various cloning vectors may be utilized. Although the preferred vector is a plasmid, the skilled artisan will appreciate that the vector may be a phage. If cloning takes place in mammalian or plant cells, viruses can also be used as vectors. If a plasmid is employed, it may be obtained from a natural source or artificially synthesized. The particular plasmid chosen should be compatible with the particular cells serving as the host, whether a bacteria such as E. coli, yeast, or other unicellular microorganism. The plasmid should also have the proper origin of replication (replicon) for the particular host cell chosen. In addition, the capacity of the vector must be sufficient to accommodate the fusion coding for both the protein molecule of interest and the binding protein.

Another feature for a plasmid cloning vector is the existence of restriction enzymes to cleave the plasmid for subsequent ligation with the foreign genes without causing inactivation of the replicon while providing suitable ligatable termini that are complementary to the termini of the foreign genes being inserted. To this end, it would be helpful for the plasmid to have single substrate sites for a large number of restriction endonucleases.

Moreover, the plasmid should have a phenotypic property that will enable the transformed host cells to be readily identified and separated from cell is which do not undergo transformation. Such phenotypic selection genes can include genes providing resistance to a growth inhibiting substance, such as an antibiotic. Plasmids are now widely available that include genes resistant to various antibiotics, such as tetracycline, streptomycin, sulfa drugs, and ampicillin. When host cells are grown in a medium containing one of these antibiotics, only transformants having the appropriate resistant gene will survive.

To prepare the chosen plasmid for ligation, preferably, it is digested with a restriction endonuclease to produce a linear segment(s) in which the two DNA strands are cleaved at closely adjacent sites to produce cohesive termini ("sticky ends") bearing 5'-phosphate- and 3'-hydroxyl groups, thereby facilitating ligation with the foreign genes. For the plasmids identified above, restriction endonucleases will produce this result.

Certain restriction enzymes (Pvu II, Bal I) may result in the formation of blunt ends. The blunt ends of the plasmid can be joined to the foreign genes with T4 DNA ligase. The methods and materials for achieving efficient cleavage and ligation are well known in the art.

Prior to being joined with the selected cloning vector, it is desirable that the foreign genes coding for the binding protein and the protein molecule be first joined together. Ideally, the gene coding for the protein molecule is treated with the same restriction endonuclease used to cleave the plasmid vector so that the appropriate termini of the gene will be compatible with the corresponding termini of the plasmid. This gene also may be treated with a second, different restriction endonuclease to prepare its opposite terminus for ligation with the binding protein gene.

The cointegrate genes are next ligated to the linearized plasmid fragment in a solution with DNA ligase. After incubation, the recirculated plasmid having the correct orientation of the cointegrate genes are identified by standard techniques, such as by gel electrophoresis.

Expression plasmid preparation is not limited by the cloning methodology used. In some embodiments, ligation-independent cloning is used (e.g., as described in Example 1). In some embodiments, expression plasmids are prepared using recombinational cloning methods (e.g., as described in U.S. Pat. Nos. 7,198,924; 7,223,576; 7,244,560; 7,351,578; 7,393,632; and 7,408,049).

D. Transformation of Recombinant DNA Plasmid

The recombinant DNA plasmids, as prepared above, are used for the transformation of host cells. Although the host cell may be any appropriate prokaryotic or eukaryotic cell, preferably it is well-defined bacteria, such as E. coli or yeast strain. Both such hosts are readily transformed and capable of rapid growth in fermentation cultures. In place of E. coli, other unicellular microorganisms can be employed, for instance fungae and algae. In addition, other forms of bacteria such as salmonella or pneumococcus may be substituted for E. coli. Whatever host is chosen, it should be one that has the necessary biochemical pathways for phenotypic expression and other functions for proper expression of the hybrid polypeptide. The techniques for transforming recombinant plasmids in E. coli strains are widely known. A typical protocol is set forth in Maniatis et al. supra.

In transformation protocols, only a small portion of the host cells are actually transformed, due to limited plasmid uptake by the cells. Thus, before transformants are isolated, the host cells used in the transformation protocol typically are multiplied in an appropriate medium. The cells that actually have been transformed can be identified by placing the original culture on agar plates containing a suitable growth medium containing the phenotypic identifier, such as an antibiotic. Only those cells that have the proper resistance gene will survive. Cells from the colonies that survive can be lysed and then the plasmid isolated from the lysate. The plasmid thus isolated can be characterized, e.g. by digestion with restriction endonucleases and subsequent gel electrophoresis or by other standard methods.

Once transformed cells are identified, they can be multiplied by established techniques, such as by fermentation. In addition, the recovered cloned recombinant plasmids can be used to transform other strains of bacteria or other types of host cells for large scale replication and expression of the fused protein.

E. Purification of the Fused Protein

The hybrid polypeptides expressed by the transformed host cell are preferably separated from all other cellular constituents and growth media by an affinity chromatography process. The column matrix is simply any substrate for which the binding protein has specific affinity. For example, Mocr has a strong interaction with DEAE-cellulose.

An extract from the transformed host cell is contacted with the column to isolate the hybrid polypeptide. The hybrid polypeptide may thereafter be eluted from the column, for example, by adding a dilute solution of a desorbing agent, which displaces the hybrid polypeptide.

F. Separation of the Protein Molecule from the Hybrid Polypeptide

The hybrid polypeptide purified from the above affinity column may be cleaved by sequence specific proteases such as a factor Xa or tobacco etch virus (TEV) protease, or by discrete chemical cleavage as occurs using, e.g., cyanogen bromide.

EXPERIMENTAL

The following examples serve to illustrate certain preferred embodiments and aspects of the present invention and are not to be construed as limiting the scope thereof.

Example 1

A. Methods and Materials

Construction and cloning of mocr. A synthetic sequence of the ocr gene was created to yield oligos with minimal dimerization potential and self-annealing. The purpose of the silent mutations contained in the synthetic sequence was to improve the efficiency of the synthetic gene construction. This sequence also incorporated mutations that change the amino acid sequence. Codon 53 has been changed from TTT to CGT and codon 77 has been changed from GTA to GAC (FIG. 1A; SEQ ID NO:3). These codon changes gave rise to the following amino acid changes: F53R and V77D. The amino acid sequence of Mocr is shown in FIG. 1B (SEQ ID NO:4).

The gene was then constructed through a combination of sequential oligo pair annealing and ligation and PCR. For sequential oligo pair annealing and ligation, the oligos were resuspended in water to 20 µM. Each oligo was then phosphorylated in a 20 µl reaction containing 2 µl ATP (10 mM), 2 µl 10× ligation buffer (NEB), 12.5 µl of the oligo, 2.5 µl H₂O and 1 µl of polynucleotide kinase. Reactions were incubated at 37° C. for one hour, then at 95° C. for ten minutes. Complementary oligo pairs were mixed and slow cooled to 37° C. to create double-stranded fragments. Adjacent fragments were then mixed in equal volume and slow cooled to 4° C. At 4° C. additional ATP was added along with 2 units of T4 DNA ligase and incubation was continued at 4° C. for one hour. Mixing of adjacent fragments at 37° C. followed by slow cooling and ligation was continued until all the fragments had been mixed. The resulting fragment was then PCR amplified using outside primers to add a BglII restriction site to the 5' end and a KpnI site to the 3' end. The resulting fragment was gel purified and cloned into pMCSG7 (Stols et al., Pro. Expr. Purif. 25 (2002) 8-15) digested with BglII and KpnI.

Cloning wild-type ocr. Bacteriophage T7 DNA was obtained from ATCC (BAA-1025-B2). Phage were produced by transfection of strain HMS174 (ATCC 47011) with resuspended DNA. The cells were grown until lysis. This broth was used to infect two 5 ml cultures of HMS174. After lysis the cell debris was collected by centrifugation. The phage were precipitated from the supernatant by the addition of PEG with incubation at 4° C. overnight followed by centrifugation. The pellets were resuspended in a total of 1 ml of PBS. A 200 µl aliquot was extracted with phenol/chloroform and the DNA was then precipitated by addition of ammonium acetate and ethanol. This DNA was used as PCR template in reactions using outside primers to add a BglII restriction site to the 5' end and a KpnI site to the 3' end. The resulting fragment was gel purified and ligated with pMCSG7. Positive clones were identified by PCR and confirmed by DNA sequencing.

Gel filtration of Ocr and Mocr. 250 mL cultures in terrific broth (TB: 6 g tryptone, 12 g yeast extract, 4% (20 ml) glycerol, 1.15 g KH₂PO₄, 6.25 g K₂HPO₄ in 500 ml distilled were grown in 1 L flasks at 37° C., 250 rpm to an OD at wavelength 600 of approximately 1. The temperature was reduced to 20° C. and after equilibration at this temperature for 1 hour the cultures were induced by addition of 200 µM IPTG. Incubation was continued at 20° C. overnight (18 hours). Cultures were centrifuged and pellets were frozen at −80° C. Cell pellets (5-6 g) were resuspended in 40 ml PBS with 0.1 mg/ml lysozyme and benzonase and lysed by sonication. Lysate was centrifuged at 20,000×g for 1 hour. Soluble fraction was batch bound overnight to 2 ml Ni-NTA agarose from Qiagen. Resin was washed with 20 mM imidazole in PBS and eluted off with 250 mM imidazole in PBS. The 10-15 ml eluate was dialyzed in 50 mM Tris pH 8.0, 150 mM NaCl, 0.1 mM EDTA, and 1 mM DTT. Gel filtration was performed using a 120 ml Superdex 75 column on an Akta Explorer FPLC. The running buffer composition was the same as the dialysis buffer.

DEAE chromatography. Soluble fraction was batch bound to 2 ml DEAE resin for 2 hours. DEAE chromatography was performed using DEAE Ceramic HyperD F resin from Pall Life Sciences. The resin was washed with 50 mM sodium phosphate and varying concentrations of NH₄Cl, from 50 mM to 400 mM, and then eluted with 50 mM sodium phosphate and varying concentrations of NH₄Cl, from 400 mM to 1 M.

High-Throughput Construct Design, Cloning, Expression and Purification.

Design. Protein sequences were analyzed for ordered and disordered regions using server based programs: Foldindex and DisEMBL. Secondary structure was predicted using Jpred. This information was overlaid with prior biochemical and functional domain information to design constructs. A full-length native construct was always included as a standard for comparison for protein production level of the various constructs. The other constructs were variations on the gene sequence, which gave rise to forms of the protein of interest that had truncations at either or both ends in different combinations. The different start and stop sites designed for the gene of interest using bioinformatic analysis were combined with each other to create a matrix of different protein forms which were tested for soluble production in *E. coli*.

Oligos for PCR construction were designed using Clonemanager (Scientific and Educational Software). The following overlaps for ligation-independent cloning (LIC) were added to each oligo: coding strand 5'TACTTCCAATCCAAT-GCN (SEQ ID NO:19) and non-coding strand 5'TTATC-CACTTCCAATGTTA (SEQ ID NO:20) or 5'TTATCCACT-TCCAATG CTA (SEQ ID NO:21). For the coding strand the last three bases are an alanine codon. N is any base. An A or T is found in this position in the highest use codons for alanine in *E. coli*.

PCR construction and cloning. The constructs were produced in 50 µl PCR reactions to which was added 5 µl 10× buffer, 1 µl of 50 mM MgSO₄, 1.5 µl of 10 mM dNTP mix, 5 µl of PCR Enhancer Solution (Invitrogen), 0.5 µl of 2.5 u/ml Platinum Pfx DNA polymerase (Invitrogen) and 0.5 µl of miniprep plasmid DNA template. The program used begins with 2.5 minutes at 94° C. followed by 30 cycles of 30 seconds at 94° C., 30 seconds at 50° C. and two minutes at 68° C. The final step is an additional 3.5 minutes at 68° C. and a reduction to 4° C. The reactions were cleaned up using MinElute 96 UF PCR purification kits by Qiagen. These were run on a Biomek FX liquid handler.

The LIC vector was linearized with SspI (New England Biolabs) at 5 units/µg DNA incubated 1.5 hours at 37° C. The protein was removed using a Qiagen PCR spin kit. The linearized DNA was processed by T4 DNA polymerase to yield single-stranded ends for annealing. The 60 µl reaction contained 1.6-2.0 µg linear DNA, 6 µl 10× buffer, 3 µl 100 mM DTT, 2.4 µl 100 mM dGTP, 1.5 µl 2.5 u/µl T4 DNA polymerase (Novagen LIC qualified), 41.1 µl dH₂0, 6 µl Template (200-300 ng/µl). These were mixed on ice and then incubated in a PCR machine for 30 minutes at 22° C., shifted to 75° C. for 20 minutes, and the temperature was reduced to 4° C.

Constructs of the genes of interest were treated with T4 DNA polymerase, to prepare them for annealing, in 20 µl reactions using 5 µl of the cleaned up PCR reaction as substrate. A 1 µl aliquot of 100 mM DTT, 0.8 µl of 100 mM dCTP, 2 µl 10× buffer and 0.5 µl of T4 DNA polymerase was added to each reaction. These were incubated as for the vector.

Annealing was carried out in 96-well plates. A 1 µl aliquot of vector was mixed with 2 µl of insert on ice. The plate was placed in a PCR machine and incubated for 10 minutes at 22° C. A 1 µl aliquot of 25 mM EDTA was added to each reaction and incubation was continued for 5 minutes at 22° C. The plate was chilled on ice and a 1 µl aliquot of each reaction was used to transform 20 µl of Z-competent XL1Blue cells. These were plated on LB agar 48-well Q-trays (Genetix) containing ampicillin for selection. Colonies were picked and grown in 1 ml of LB overnight in 96-well deep well blocks and then plasmid DNA was miniprepped from these cultures using Perfect Prep 96 Vac purification kits by Eppendorf on the Biomek FX. Positives clones were identified by PCR analysis.

Expression. A 1 µl aliquot of the miniprep DNA for each positive clone was used to transform competent Rosetta2 cells in 96-well plates. The recovered transformation mixes were used to inoculate 1 ml of LB containing ampicillin and chloramphenicol as selective agents. These were grown overnight at 37° C. and used to both create glycerol stocks and inoculate 0.5 ml of terrific broth in a 96-well deep well block. The TB block was grown at 37° C. and shaking at 400 RPM to an $OD_{600}$ of approximately 1. The temperature was reduced to 20° C. and after equilibration at this temperature for 1 hour the cultures were induced by addition of IPTG to the specified concentration. Incubation was continued at 20° C. overnight (18 hours). Cultures were frozen at −80° C.

High-throughput purification. Frozen culture blocks were thawed at 25° C. A 1.26 g bottle of CelLytic Express (Sigma) was resuspended in 5 ml of PBS. A 50 µl aliquot of CelLytic was added to each well of the 96-well deep well block. These were incubated at 25° C. with shaking for 20 minutes for lysis. These were transferred to 1.1 ml Axygen minitubes and centrifuged for 10 minutes at 20,000×g. The soluble fraction was transferred to a 96-well deep well block containing 120 ml of a slurry of 75% PBS and 25% Ni-NTA Agarose from Qiagen. Protein was allowed to batch bind to resin for one hour at 4° C. The purification was performed on a Biomek FX. The resin and soluble fraction were transferred to a Whatman 96-well 2 ml glass filled 10 µm polypropylene filter. The resin was washed six times by 400 µl of 20 mM imidazole in PBS. The protein was eluted by 250 mM imidazole in PBS.

TEV cleavage of the Mocr-Med15 fusion and purification by size exclusion chromatography. The soluble fraction from cell lysates was batch bound to 2 ml Ni-NTA resin. The fusion protein was eluted with three 2 ml aliquots of 100 mM Tris (pH 7.5), 100 mM NaCl, 10 mM b-mercatoethanol, 10% glycerol, and 300 mM immidizole. The three elutions were pooled and dialyzed in the presence of tobacco etch virus (TEV) protease overnight (18 hr) at 4° C. in 50 mM Tris (pH 7.5), 100 mM NaCl, 10 mM b-mercatoethanol, and 10% glycerol. Typically the TEV protease was added at a ratio of roughly 1 to 20-25 mg of protease to mg of protein of interest using a 1 mg/ml stock of protease. For this particular experiment there was 50 mg of Mocr-Med15 fusion and 2 mg of TEV protease present. Cleaved protein was then subjected to size exclusion chromatography using a Superdex 75 column on an Akta Explorer FPLC. The Med15 containing fractions were pooled and concentrated using a Vivascience 30K centrifugal filter to a final concentration of 10 mg/ml.

Sample analysis. All analysis of PCR and high-throughput protein expression samples was done using a Labchip90 instrument (Caliper). The protein obtained from DEAE-purification trials was analyzed by SDS-PAGE using 26 lane 4-20% Tris-Gly gels followed by staining with Bio-Safe Coomassie (BioRad).

B. Results

Monomerization of Ocr protein. Gene 0.3 or ocr, is the first gene found in the linear bacteriophage T7 genome, and is also the first gene transcribed upon phage entry into the host cell. The protein encoded by ocr is an inhibitor of *E. coli* restriction enzymes (Kruger et al., Mol. Gen. Genet. 153 (1977) 99-106). Ocr protein inhibits *E. coli* type I restriction enzyme by forming an extended dimer that mimics B-form DNA (Walkinshaw et al., Molecular Cell 9 (2002) 187-194). The dimer binds the restriction enzyme in competition with the DNA substrate. The binding affinity between Ocr and EcoKI is extremely strong, with a dissociation constant estimated at 100 pM (Atanasiu et al., Nucleic Acids Res. 29 (2001) 3059-3068). Mutations were introduced into Ocr to disrupt dimer formation to prevent fusion proteins from being bound by the restriction enzymes as well as to reduce the possibility that dimerization could promote formation of large aggregates when Ocr is fused to aggregation-prone proteins.

Figure 2:
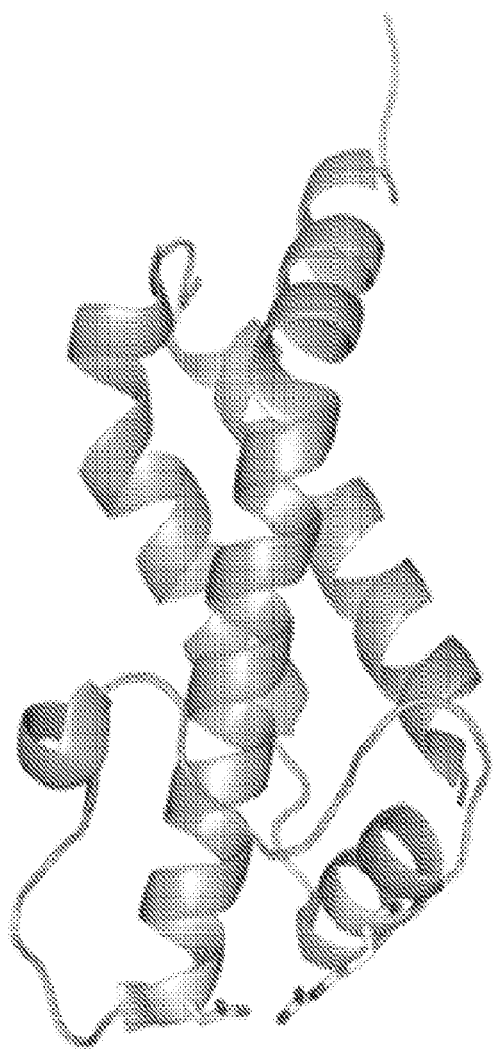
FIG. 2 shows a crystal structure of Mocr. The crystal structure of Ocr deposited in the PDB (1S7Z.pdb) was used to produce this structure.

The small interface between the Ocr monomers is composed of nonbonded hydrophobic contacts and no hydrogen bonds (Walkinshaw et al., supra). Phe 53 of one monomer appears as a "knob" that fits into a "hole" surrounded by Ala 50, Ser 54, Met 56, and Ala 57 of the other monomer. A second contact site occurs between Val 77 of the two monomers. To disrupt this interface with the smallest number of mutations, Phe53 was substituted with arginine. The charged amino acid should disfavor the insertion of the "knob" into the hydrophobic "hole". Val 77 was substituted with aspartic acid to replace the van der Waals interaction with charge repulsion between the acidic side chains. The basic arginine and the aspartic acid were designed to be close enough to potentially establish a salt bridge, which may assist in stabilizing the monomeric structure (FIG. 2). A synthetic version of the ocr gene was designed to introduce these mutations (FIG. 1).

The gene sequence shown in FIG. 1A was constructed and cloned in frame into vector pMCSG7 (Stols et al., supra). The resulting vector, pMocr (monomeric ocr), has a T7 promoter linked to a coding sequence for a $His_6$-tag, a short spacer followed by the mocr sequence and a sequence coding for a TEV cleavage site at the end (FIG. 3). A ligation-independent cloning (LIC) site in the DNA encodes a portion of the tobacco etch virus (TEV) cleavage site. The native ocr gene was also inserted into the same sites in pMCSG7 for comparison with the mutated version.

Figure 4:
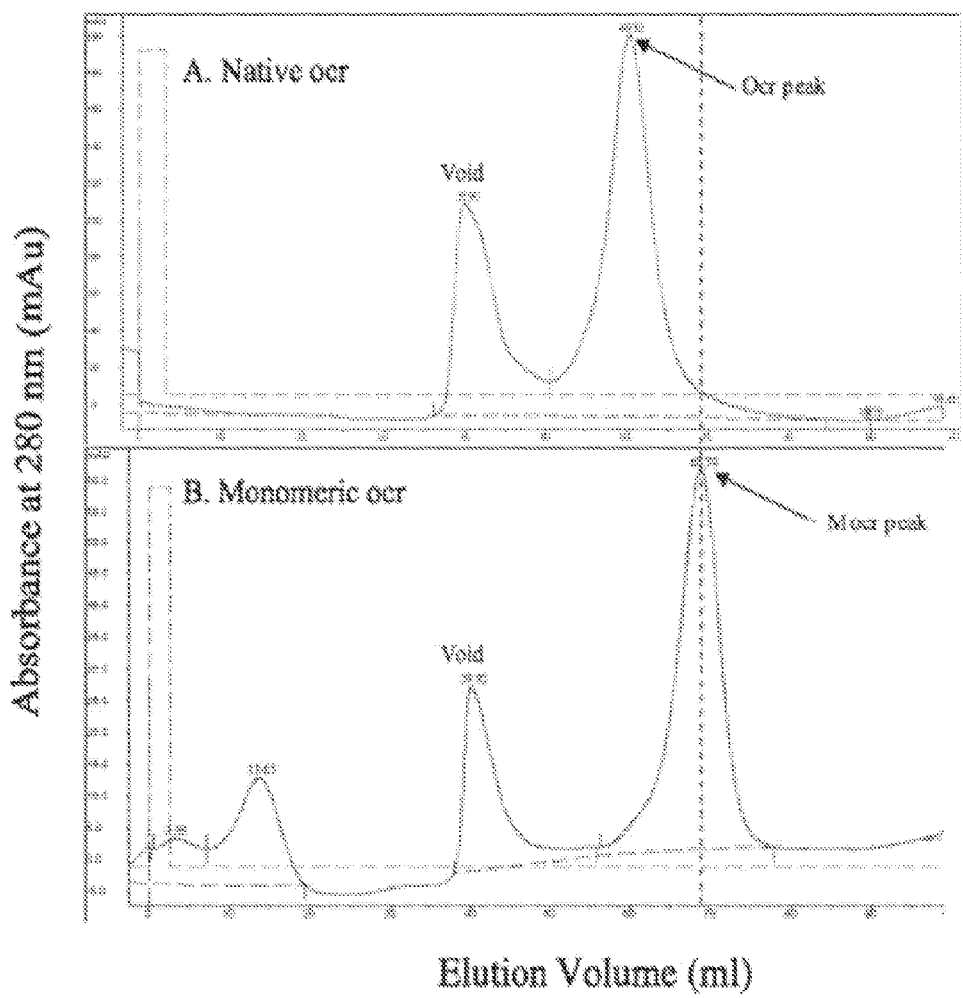
FIG. 4 shows SEC profiles for native (A) and monomeric (B) Ocr proteins.

The two forms of Ocr were produced in BL21 (DE3) cells and purified by nickel chelate chromatography then subjected to size exclusion chromatography. FIG. 4A is the profile for size exclusion chromatography of the native Ocr protein, which should run as a dimer under non-denaturing conditions. Native Ocr elutes from the size exclusion column at a calculated molecular weight of 35 kDa. The predicted molecular weight for the native Ocr protein in pMCSG7 is 16.6 kDa, which would yield a dimer of 33.3 kDa. The native protein appears to be a dimer under these conditions. When Mocr protein is run on the same size exclusion resin under identical conditions the elution peak is shifted to a later volume (69 ml versus 60 ml, FIG. 4B). The Mocr protein elutes from the size exclusion column at a calculated molecular weight of 21 kDa. The predicted molecular weight for the Mocr protein as produced from the pMCSG7 vector is 16.7 kDa. This appears to be monomeric under these conditions.

When the Mocr is cleaved from passenger protein using TEV protease during the purification of fusion proteins the released Mocr elutes from gel filtration at a calculated molecular weight between 16 and 20 kDa. Thus, the Mocr protein reproducibly behaves as a monomer in diverse contexts.

Mocr fusion has solubilizing activity. The Mocr fusion was used with a variety of target proteins (A through D below) and compared to several others fusion tags. The objectives for target protein production ranged from biochemical characterization to high-throughput screening for ligands to solving the structure by crystallography or NMR. Four representative target proteins were included in this study (Table 1).

A. Caveolin is found in caveolae, vesicular invaginations of the plasma membrane. Caveolae function in vesicle trafficking, cholesterol homeostasis, signal transduction and tumor suppression. Caveolin has several distinct domains, an N-terminal intercellular domain, which has a phosphorylation site, an oligomerization domain and a transmembrane domain. Recombinant caveolin is produced primarily in eukaryotic cells although bacterial production of the N-terminal domain as a glutathione-S-transferase (GST) fusion protein has been reported (Fernandez et al., Proc. Natl. Acad. Sci. 99 (2002) 11193-1198). The goal was to find stable, soluble forms of the caveolin protein as wild type and also as phosphorylation mutants and as mutants of the oligomerization domain. Most of the constructs were truncations although full-length versions were also tried.

B. Bryostatin is an anti-cancer compound synthesized by an uncultured symbiont of a marine invertebrate (Davidson et al., Appl. Environ. Microbiol. 67 (2001) 4531-4537). Characterizing the activities of the biosynthetic enzymes in the pathway of bryostatin allows for the development of novel combinations of enzymes that would yield a wider variety of bryostatin analogues with different therapeutic properties. The full-length version of an acyl transferase from this pathway did not yield soluble protein when expressed in E. coli. The goal for this project was to obtain soluble protein for biochemical characterization and for structural studies.

C. The penton and fiber knob proteins of adenovirus are found at the vertices of the icosahedral capsid. These proteins are involved in binding cellular receptors including integrins, triggering internalization via endocytosis. The mouse adenovirus type 1 (MAV-1) fiber knob protein has a unique loop sequence not found in other homologs. To facilitate both biochemical and structural characterization, a variety of constructs of each gene were designed for expression in E. coli.

D. Noroviruses, members of the Caliciviridae family, infect primarily humans but also pigs, cattle and mice. Human noroviruses are the major cause of nonbacterial epidemic gastroenteritis worldwide resulting in substantial morbidity and economic loss but no drugs or vaccines are available for treatment. Virus-receptor interaction and virus entry have become attractive targets for antiviral therapies. To facilitate this goal constructs encoding full-length or truncated versions of the mouse norovirus (MNV) major capsid gene VP1 or its two domains ("shell" and "protruding" [P]) were designed for expression in E. coli.

The different constructs for each gene were cloned into several fusion vectors and expression was carried out in a Rosetta BL21 (DE3) strain of E. coli. All the vectors were based on the pMCSG vectors (Fernandez et al., Proc. Natl. Acad. Sci. 99 (2002) 11193-1198) and have a sequence encoding a $His_6$ tag followed by either a spacer or a fusion tag and then a TEV cleavage site encoding sequence adjacent to the gene of interest. The cultures were subjected to chemical lysis and the insoluble fractions were separated by centrifugation. The proteins of interest were purified by chromatography on nickel resin in a 96-well plate format. The eluates were analyzed for protein using a Caliper Labchip90. A protein was considered soluble if it was detected at >20 ng/mL by the Labchip90 analysis. This level of production would be roughly equivalent to 2 mg of purified protein per liter of culture.

Figure 5:
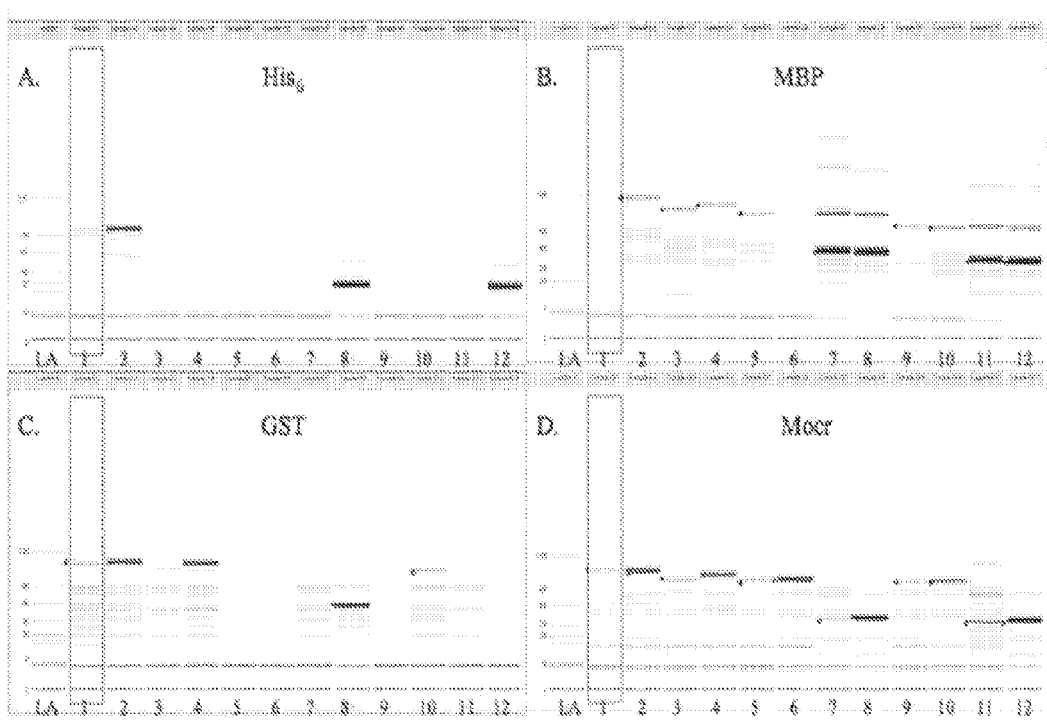
FIG. 5 shows Labchip 90 analysis of MNV major capsid protein constructs for soluble expression in different fusion vectors. The data is shown as a gel representation similar to SDS-PAGE stained with coomassie blue. Panel A, $His_6$ fusions; panel B, MBP fusions; panel C, GB1 fusions; and panel D, Mocr fusions. The first lane (labeled LA) in each panel is a protein molecular weight ladder ranging from 1 to 120 kD. Each lane (numbered 1-12) is the protein produced from a different construct of the MNV major capsid protein gene. The dot identifies the protein migrating at the expected molecular weight for each construct and fusion. The same constructs are shown for each fusion tag.

Only 7 of the 98 constructs were detectable in the soluble fraction when a $His_6$ tag was used alone. For all protein targets, Mocr displayed solubilizing activity (Table 1) comparable to MBP. By comparison, fusions with GST or immunoglobulin-binding domain of streptococcal protein G (GB1) displayed lower efficiency in solubilizing the constructs. The data for a representative set of samples (MNV construct fusions) from the Labchip analysis of soluble protein in the eluate from the nickel resin purification step are shown in FIG. 5. The dot identifies the protein at the expected molecular weight for each construct. Although the pattern of solubilization between Mocr and MBP was similar, the yield for individual constructs varied among the fusion tags. In several of the MBP lanes (7, 8, 11 and 12) there appear to be multimers of the protein of interest forming. This has been observed in samples of high protein concentration. The standard Labchip sample buffer does not contain a reducing agent and it is contemplated that these multimers are the result of disulfide bond formation between cysteines in the passenger portion of the fusion protein.

Mocr can function as a purification handle. The Ocr protein is not a standard affinity tag, however it has a strong interaction with DEAE-cellulose resin. In the initial reported purification (Mark and Studier, J. Biol. Chem. 256 (1981) 2573-2578) Ocr was bound to DEAE resin in the presence of 0.3 M $NH_4Cl$, a condition at which few other proteins in the E. coli lysate bound to the resin. The Ocr protein was then eluted at 95% purity with 0.5-0.6 M $NH_4Cl$.

Figure 6:
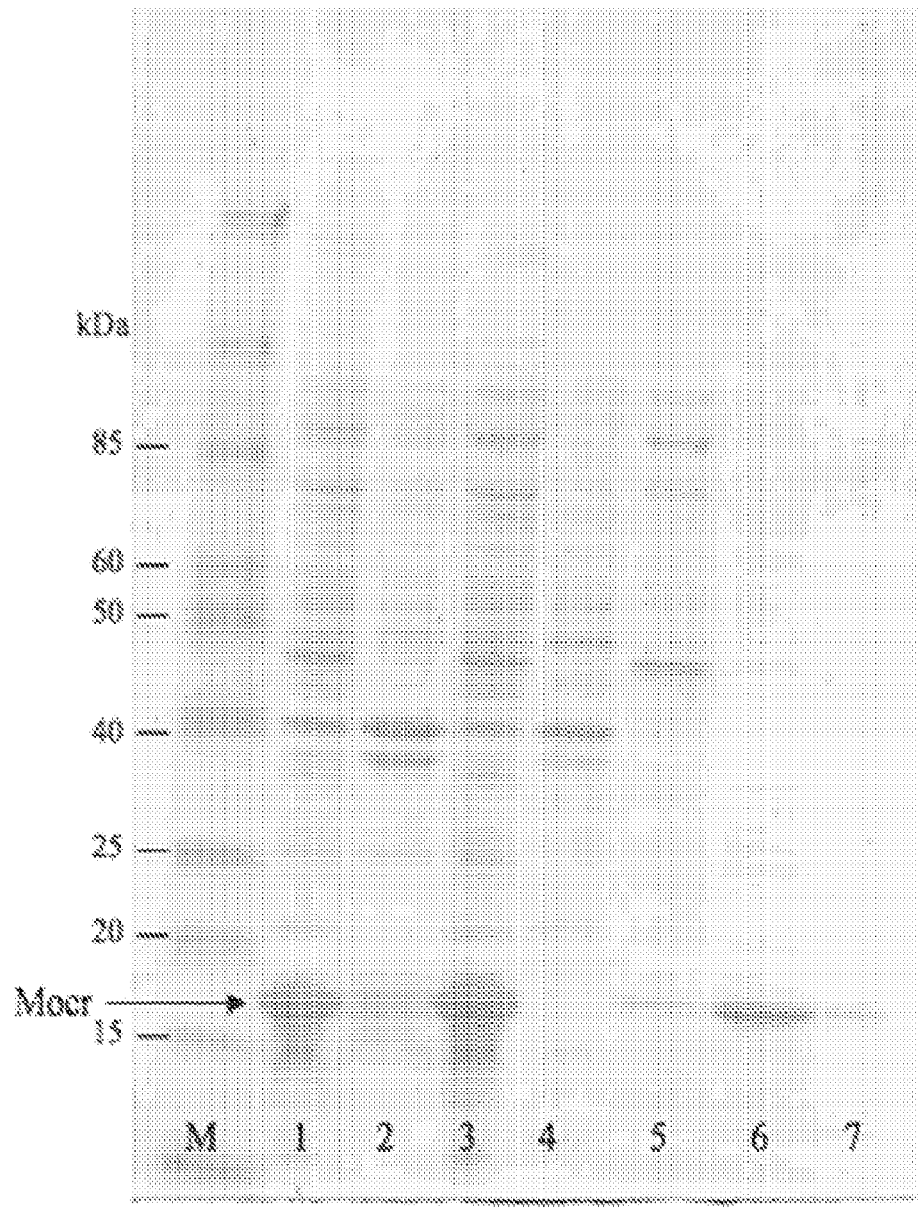
FIG. 6 shows SDS-PAGE analysis of wash and elution conditions for purification of Mocr protein on DEAE-cellulose resin. Molecular weight marker (M), whole cell extract (1), insoluble fraction (2), soluble fraction (3), flow-through (4), 200 mM $NH_4Cl$ wash (5), 600 mM $NH_4Cl$ elution (6), resin (7). The position of Mocr protein is identified by the arrow.

The ability to purify Mocr as configured in the fusion vector from bacterial lysates using DEAE-cellulose was investigated. A matrix of wash and elution conditions was run to find the optimal combination for yield and purity. In these experiments, the Mocr encoded by the vector described above behaved similarly to the native Ocr during purification by DEAE-cellulose. Optimal conditions were slightly different than those described previously (Mark and Studier, supra), with a 200 mM $NH_4Cl$ wash followed by a 600 mM $NH_4Cl$ elution yielding the best results. The purifications were repeated at a larger scale to confirm these results (FIG. 6). The purity of the eluted protein was estimated at greater than 80%. Treatment of the resin with SDS to remove any uneluted protein showed a small amount did remain bound after the elution (FIG. 6, lane 7).

Figure 7:
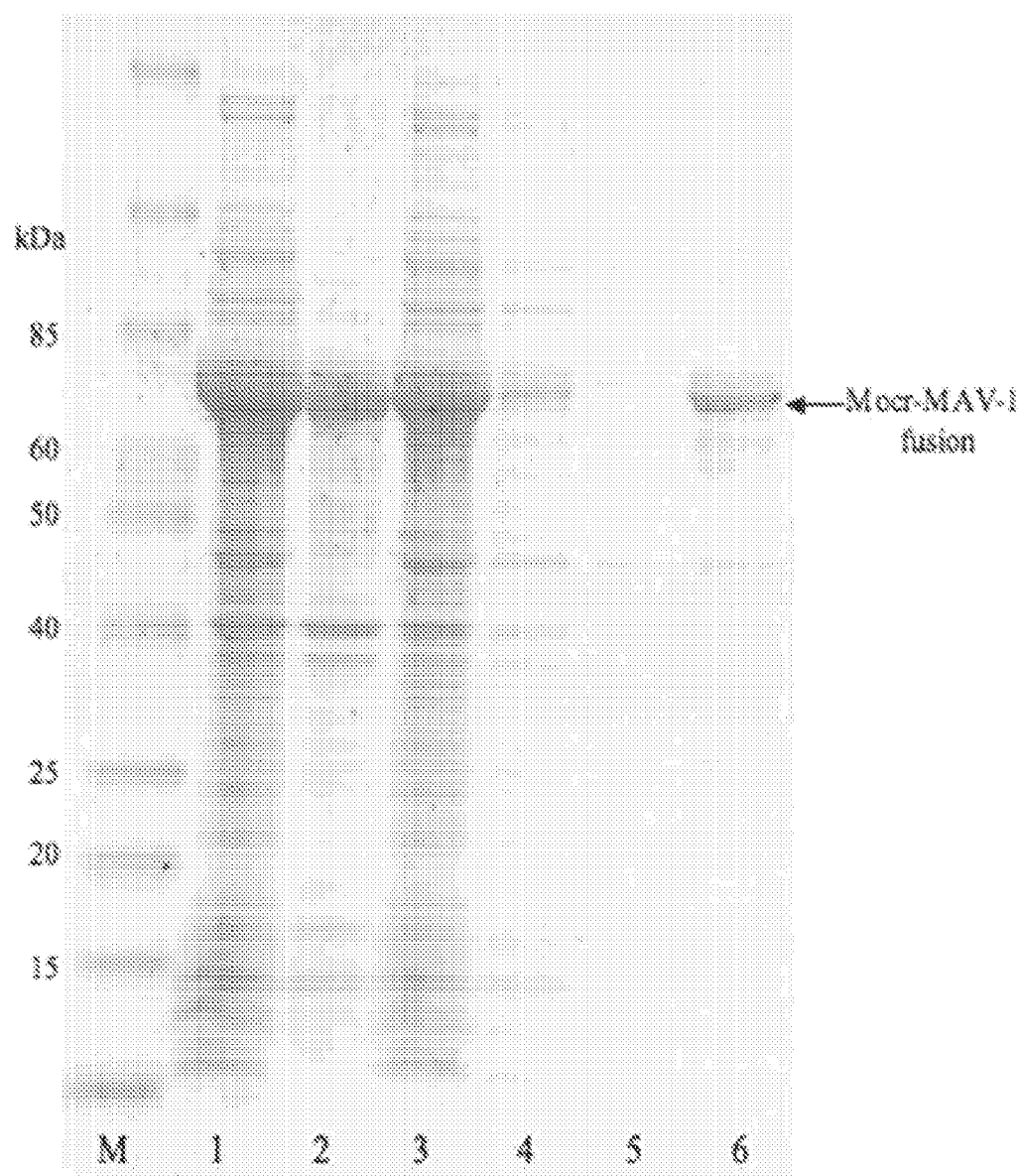
FIG. 7 shows SDS-PAGE analysis of DEAE-cellulose purification fractions for a Mocr-MAV-1 fusion protein. Molecular weight marker (M), whole cell extract (1), insoluble fraction (2), soluble fraction (3), flow-through (4), wash (5), elution with 600 mM $NH_4Cl$ (6). Arrow indicates the position of the fusion protein.

The effect of a passenger protein on the DEAE-cellulose purification profile of Mocr (FIG. 7) was next examined. For these experiments, fusions of Mocr with one of the MAV-1 penton protein constructs (pI=7.3) used in Table 1 were utilized. The fusion was produced as described above for Mocr alone. The soluble fraction was batch bound to DEAE-cellulose resin, poured into a column, washed with a buffer containing 200 mM $NH_4Cl$ and eluted with one volume of buffer containing 600 mM $NH_4Cl$. The eluted fusion protein displays a high level of purity, greater than 80%. This shows that the Mocr protein may function as a purification handle similar to other affinity fusion tags.

Figure 8:
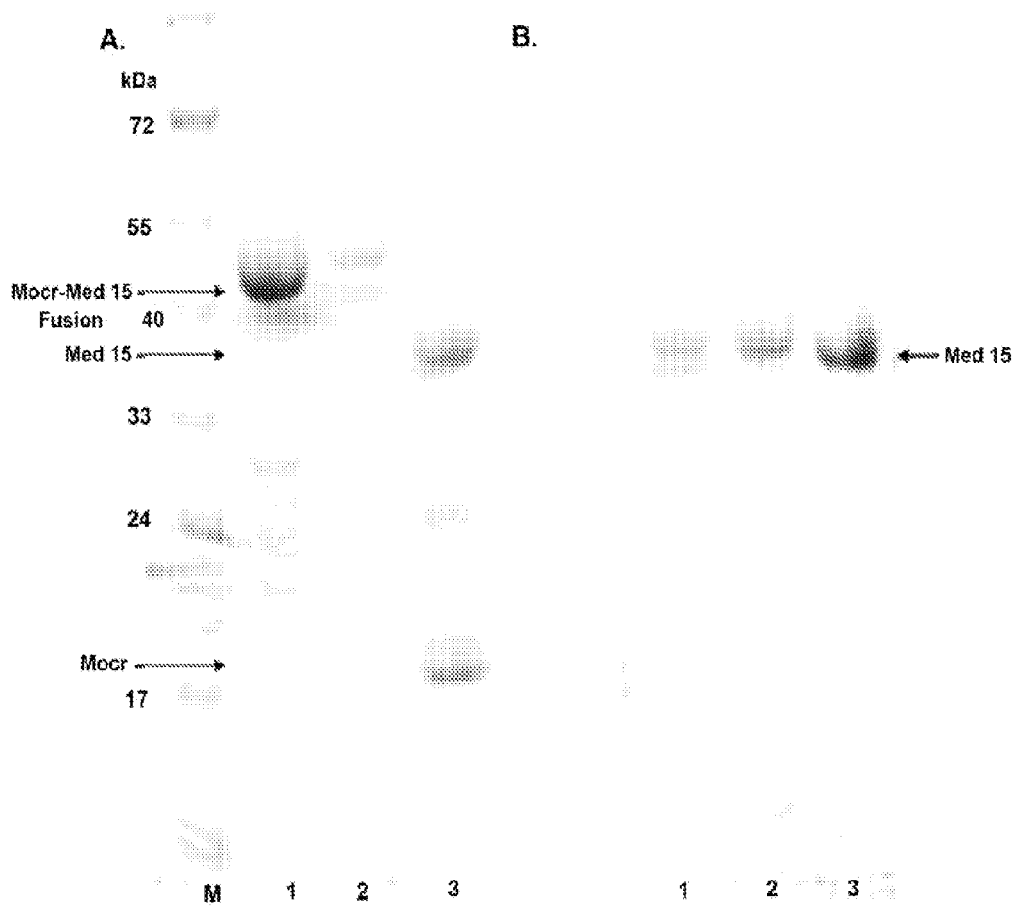
FIG. 8 shows SDS-PAGE analysis of TEV cleavage of a Mocr-Med15 fusion protein. A. Molecular weight marker (M), first imidazole elution from NiNTA (1) third imidazole elution from NiNTA (2) TEV cleavage of fusion (3). B. Gel filtration fractions (1), (2), pooled fractions concentrated 5× (3). The proteins are identified with arrows.

Cleavage of the passenger protein from the Mocr fusion. Med15 is a component of the Saccharomyces cerevisiae Mediator complex that is involved in activation of transcription (Bjorklund and Gustafsson, TRENDS in Biochemical Sciences 30 (2006) 240-244). In an effort to define interaction domains within this protein, 72 different constructs were made which were fused with both MBP and Mocr. In some applications, removal of MBP after cleavage from the fusion proved difficult using affinity chromatography but could be accomplished by size-exclusion chromatography. Generally, in cases where the passenger and fusion tag are of similar size, this option is not available. This was the case with this Med15 construct; cleaved MBP could not be efficiently removed from the Med15 portion of the fusion. In pMCSG9 (Donnelly et al., supra), MBP is fused to a His$_6$ tag allowing the MBP to be removed from the passenger protein after cleavage of a fusion protein by passing the preparation over a nickel column. A large portion of the Med15 was retained along with the MBP when this was done using this fusion construct, dramatically reducing the yield. The similarity of the molecular weights of the MBP and this Med15 construct did not allow for efficient separation using size exclusion chromatography. This Med15 protein-Mocr fusion was tested for cleavage by the tobacco etch virus (TEV) protease and purification of the Med15 protein construct away from the Mocr portion of the fusion (FIG. 8). Cleavage of the Med15-Mocr fusion by TEV protease was complete; no intact fusion protein was visible after the reaction (FIG. 8A). The Med15 protein construct can then be purified away from the Mocr portion of the fusion by size-exclusion chromatography (FIG. 8B).

The use of Mocr with a passenger protein of this size allows for greater flexibility in this step of the purification protocol than a corresponding MBP fusion would allow.

Comparison of Mocr with another small fusion protein. Small fusion tags are desirable for many applications in which the fusion is left intact. Mocr was compared with GB1, another small fusion partner (Huth et al., Protein Science 6 (1997) 2359-2364; Koenig et al., J. of Biomolecular NMR 26 (2003) 193-202), for the ability to produce soluble variants of S11, a small (129 amino acids) ribosomal protein from *E. coli*. The *E. coli* protein was fused with His$_6$ (pMCSG7), GB 1 (cloned into pMCSG7 identically to mocr) or Mocr. The Mocr fusion solubilized almost all of the variants and yielded consistently higher levels of protein after nickel purification (Table 2).

TABLE 1

Solubilization of passenger proteins by Mocr fusions

| Protein | Total constructs (Mol. Wt. range[a]) | His | GST | MBP | GB1 | Mocr |
|---|---|---|---|---|---|---|
| Caveolin | 22 (7-20.5 kDa) | 0 | | 6 | 0 | 5 |
| Acyl trans. | 32 (31-100 kDa) | 0 | | 17 | | 14 |
| MAV-1 | 24 (25-55 kDa) | 2 | | 24 | 19 | 18 |
| MNV | 20 (18-59 kDa) | 5 | 7 | 18 | | 20 |

[a]The molecular weight range is of the constructs for each protein and only includes the passenger protein and not the fusion tag. The largest molecular weight corresponds to the full-length native form of the protein and the others represent a matrix of truncations at either or both ends of the protein.

TABLE 2

Comparison of soluble protein yields between small fusion tags

| | Eluate Conc ng/uL (Total nmol)[b] | | |
|---|---|---|---|
| Construct[a] | His | GB1 | Mocr |
| T1-A | 210 (750) | 395 (1000) | 321 (584) |
| T1-B | 43 (160) | | 596 (1,084) |
| T1-C | 4 (13) | 304 (714) | 248 (428) |
| T1-D | 17 (64) | 39 (98) | 231 (420) |

TABLE 2-continued

Comparison of soluble protein yields between small fusion tags

| | Eluate Conc ng/uL (Total nmol)[b] | | |
|---|---|---|---|
| Construct[a] | His | GB1 | Mocr |
| T1-E | 20 (74) | | |
| T1-F | 5 (17) | | 36 (62) |
| T3-A | 124 (462) | 485 (1,227) | 776 (1,412) |
| T3-B | 25 (93) | 491 (1,242) | 398 (720) |
| T3-D | 25 (93) | 77 (195) | 315 (573) |
| T3-E | | | 78 (142) |
| T4-A | 188 (700) | 381 (964) | 375 (680) |
| T4-B | 32 (119) | 254 (642) | 485 (882) |
| T4-D | 15 (56) | 31 (78) | 255 (464) |
| T4-E | 158 (588) | 36 (91) | 245 (446) |

[a]T1, T3 and T4 represent three different mutant versions for the S11 ribosomal protein gene from *E. coli*. T1 contains a single amino acid substitution from the native sequence, T3 contains two and T4 contains eight. The same start and stop sites were used for each template but the C. and F. combinations were not made for T3 and T4.
[b]96-well expression cultures followed by chemical lysis and metal-affinity chromatography were run as described in Materials and Methods. The samples were then run on the Labchip 90 protein chip. The protein quantitation from the Labchip data was downloaded into an Excel file and is shown here. The total nmols for each sample was then calculated using these concentrations, the total volume and the molecular weight of each fusion protein.

Example 2

Figure 14:
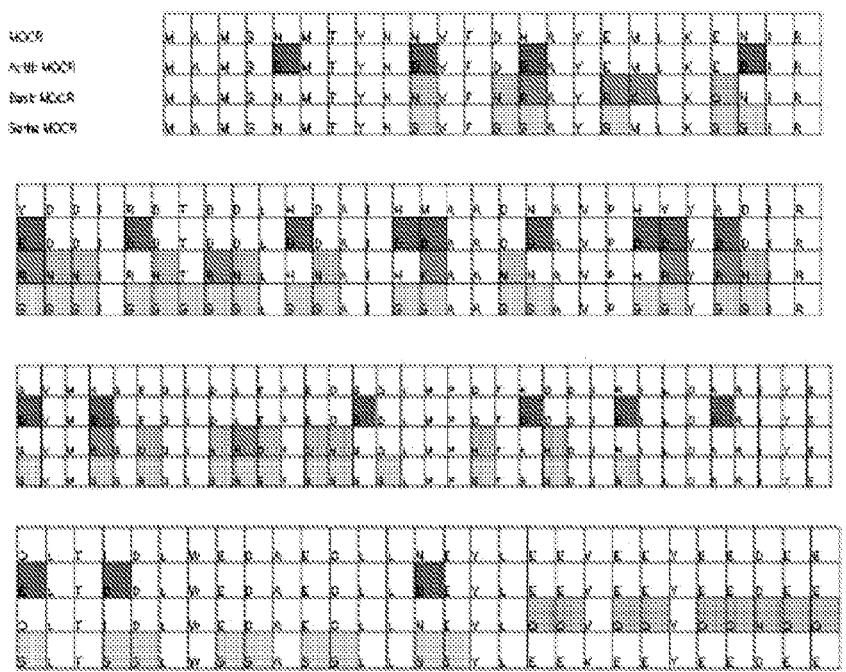

Variants of the Mocr gene were designed and tested. These variants give rise to charged proteins with 1) a more acidic pI than Mocr, or 2) a basic pI, or 3) an uncharged protein in which serine has been substituted for the native amino acids (FIG. 14). A commercial vendor synthesized these gene sequences and the synthesized sequences were cloned into pMCSG7 (see, e.g., Example 1).

Expression trials were carried with these genes alone in absence of fusion to a partner protein sequence using methods described in Example 1. All three versions of the Mocr protein were produced in *E. coli*. The acidic version was found only in the soluble fraction. The basic version was partitioned between the soluble and insoluble fractions of the cell. The serine rich version was found only in the insoluble fraction of the cell.

Example 3

In some embodiments, additions, deletions, or substitutions are made to Mocr-encoding nucleic acid sequences to alter the linker region between the Mocr protein tag and the passenger protein with the intent of providing amino acid linker sequence with rigid structure. While the present invention is not limited to any particular mechanism, and an understanding of the mechanism is not necessary to practice the present invention, it is contemplated that inclusion of such rigid linker structure between the Mocr protein tag and the passenger protein facilitates crystallization of the resulting fusion protein. The ligation-independent cloning region in the original Mocr construct and the carboxyl terminal unstructured region identified in the Ocr structure is removed (FIG. 15). The last two amino acids in the final alpha helix of Ocr are leucine and glutamate. The coding sequence in the gene for these amino acids is changed to yield an XhoI restriction site. A passenger protein coding sequence is cloned into this site and one of the downstream restriction sites. The resulting fusion protein thus includes a rigid link between the end of the Mocr protein and then beginning of the passenger protein, which may facilitate the crystallization of the fusion. Another variation removes the His$_6$ coding sequence at the beginning of the Mocr gene to further reduce the unstructured regions in the fusion protein.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A composition comprising a variant ocr nucleic acid sequence, wherein said variant nucleic acid sequence encodes a monomeric Ocr protein with F53R and V77D mutations of native Ocr protein.

2. The composition of claim 1, wherein said monomeric Ocr protein further comprises altered amino acids at one or more positions selected from the group consisting of 50, 54, 55, 56, and 57.

3. The composition of claim 1, wherein said monomeric Ocr protein has the amino acid sequence of SEQ ID NO:2.

4. The composition of claim 1, wherein said variant ocr nucleic acid sequence has the nucleic acid sequence of SEQ ID NO:1.

5. The composition of claim 1, wherein said variant ocr nucleic acid sequence is fused to a nucleic acid sequence encoding a protein of interest.

6. The composition of claim 5, wherein said variant ocr nucleic acid sequence encodes a monomeric Ocr-protein of interest fusion protein.

7. The composition of claim 5, wherein said nucleic acid sequence is in an expression vector.

8. The composition of claim 7, wherein said expression vector is in a host cell.

9. The composition of claim 8, wherein said host cell is *E. coli*.

10. An expression vector comprising a variant ocr nucleic acid sequence, wherein said variant nucleic acid sequence encodes a monomeric Ocr protein.

11. The expression vector of claim 10, wherein said variant ocr nucleic acid sequence is fused to a nucleic acid sequence encoding a protein of interest.

12. The expression vector of claim 11, wherein said variant ocr nucleic acid sequence encodes a monomeric Ocr-protein of interest fusion protein.

13. The composition of claim 1, wherein said variant nucleic acid sequence encodes a monomeric Ocr protein with a pI that is more acidic than that of a monomeric Ocr protein with F53R and V77D mutations.

14. The composition of claim 13, wherein said monomeric Ocr protein with acidic pI comprises N4D, N9D, H13D, N21D, Y24E, R28D, H34D, H38D, M39D, N43D, H47D, Y48D, A50D, S54D, A57D, S68D, K75D, R79E, A83D, Q88E, I91D, and N102D mutations.

15. The composition of claim 1, wherein said variant nucleic acid sequence encodes a monomeric Ocr protein with a pI that is more basic than that of a monomeric Ocr protein with F53R and V77D mutations.

16. The composition of claim 15, wherein said monomeric Ocr protein with basic pI comprises D12N, H13R, E16R, M17K, E20Q, Y24R, D25N, D26N, D29N, D31R, D32N, D35N, M39K, M42N, Y48R, A50R, D51N, A57R, E59Q, D62H, L63R, E64Q, E66Q, D67H, D73H, D76H, E106Q, E107Q, E109Q, E110Q, E112Q, E113Q, D114N, E115Q, and E116Q mutations.

17. The composition of claim 1, wherein said variant nucleic acid sequence encodes a monomeric Ocr protein with a pI that is more uncharged than that of a monomeric Ocr protein with F53R and V77D mutations.

18. The composition of claim 17, wherein said monomeric Ocr protein with a pI that is more uncharged than that of a monomeric Ocr protein with F53R and V77D mutations comprises N9S, D12S, H13S, E16S, E20S, N21S, Y42S, D25S, D26S, R28S, D29S, T30S, D31S, D32S, H34S, D35S, H38S, M39S, D42S, N43S, H47S, Y48S, A50S, D51S, A57S, E59S, D62S, L63S, E64S, E66S, D67S, G69S, D73S, D76S, R79S, Q88S, I91S, D92S, E95S, D96S, E98S, D99S, N102S, and E103S mutations.

19. A method of expressing a protein of interest, comprising a) delivering an expression vector comprising an expression construct comprising a variant ocr nucleic acid sequence encoding a monomeric Ocr protein with F53R and V77D mutations of native Ocr protein fused to a nucleic acid sequence encoding a protein of interest to a host cell; and b) expressing said expression construct under conditions such that a fusion protein comprising monomeric Ocr protein fused to a gene of interest is expressed.

20. The method of claim 19, further comprising the step of purifying said fusion protein.

21. The method of claim 20, wherein said purifying comprises DEAE chromatography.

22. The method of claim 19, further comprising the step of cleaving said fusion protein to generate a monomeric Ocr protein and a protein of interest.

23. The method of claim 22, wherein said cleaving comprises contacting said fusion protein with tobacco etch virus (TEV) protease.

24. The method of claim 19, wherein said monomeric Ocr protein further comprises altered amino acids at one or more positions selected from the group consisting of 50, 54, 55, 56, and 57.

25. The method of claim 19, wherein said monomeric Ocr protein has the amino acid sequence of SEQ ID NO:2.

26. The method of claim 19, wherein said variant ocr nucleic acid sequence has the nucleic acid sequence of SEQ ID NO:1.

* * * * *

UNITED STATES PATENT AND TRADEMARK OFFICE
CERTIFICATE OF CORRECTION

PATENT NO.        : 8,357,511 B2
APPLICATION NO.   : 13/055199
DATED             : January 22, 2013
INVENTOR(S)       : Brown et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 86 days.

Signed and Sealed this
First Day of September, 2015

Michelle K. Lee
*Director of the United States Patent and Trademark Office*